US009746624B2

(12) United States Patent
Ohara

(10) Patent No.: US 9,746,624 B2
(45) Date of Patent: Aug. 29, 2017

(54) OPTICAL CONNECTOR FOR ENDOSCOPE

(71) Applicant: OLYMPUS CORPORATION, Tokyo (JP)

(72) Inventor: Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/055,774

(22) Filed: Feb. 29, 2016

(65) Prior Publication Data
US 2016/0178860 A1    Jun. 23, 2016

Related U.S. Application Data

(63) Continuation of application No. PCT/JP2014/067578, filed on Jul. 1, 2014.

(30) Foreign Application Priority Data

Aug. 29, 2013 (JP) .................................. 2013-178688

(51) Int. Cl.
*G02B 6/42* (2006.01)
*G02B 6/38* (2006.01)
(Continued)

(52) U.S. Cl.
CPC .......... *G02B 6/423* (2013.01); *A61B 1/00126* (2013.01); *G02B 6/3616* (2013.01);
(Continued)

(58) Field of Classification Search
CPC .... G02B 6/423; G02B 6/3616; G02B 6/3807; G02B 6/3825; G02B 6/3846;
(Continued)

(56) References Cited

U.S. PATENT DOCUMENTS 5,721,798 A    2/1998 Kanda et al.
6,450,695 B1    9/2002 Matsumoto
(Continued)

FOREIGN PATENT DOCUMENTS

JP    S56-70748 A    6/1981
JP    H05-264855 A    10/1993
(Continued)

OTHER PUBLICATIONS

English translation of International Preliminary Report on Patentability dated Mar. 10, 2016 together with the Written Opinion received in related International Application No. PCT/JP2014/067578.

(Continued)

*Primary Examiner* — John M Bedtelyon
(74) *Attorney, Agent, or Firm* — Scully, Scott, Murphy & Presser, P.C.

(57) ABSTRACT

An optical connector for an endoscope has a first holding member which holds a first waveguide therein, a second holding member which holds a second waveguide therein and replaceable replacement members which intervenes between the first holding member and the second holding member so that replacement waveguides intervenes between the waveguides and is optically coupled to the waveguides. The optical connector has attachment members and a positioning mechanism which positions the holding members and the replacement members relative to one another.

20 Claims, 8 Drawing Sheets

(51) Int. Cl.
*G02B 23/26* (2006.01)
*G02B 6/36* (2006.01)
*A61B 1/00* (2006.01)

(52) U.S. Cl.
CPC ......... *G02B 6/3807* (2013.01); *G02B 6/3825* (2013.01); *G02B 6/3846* (2013.01); *G02B 6/3885* (2013.01); *G02B 23/26* (2013.01); *G02B 6/3853* (2013.01); *G02B 6/3882* (2013.01)

(58) Field of Classification Search
CPC .... G02B 6/3885; G02B 23/26; G02B 6/3853; G02B 6/3882; G02B 23/24; G02B 23/2407; G02B 23/2446; G02B 6/2469
See application file for complete search history.

(56) References Cited

U.S. PATENT DOCUMENTS 8,419,622 B2 * 4/2013 Shimotsu ................ A61B 1/07
385/34

| | | | |
|---|---|---|---|
| 2003/0152326 A1 | 8/2003 | Morimoto et al. | |
| 2012/0076458 A1 | 3/2012 | Lin et al. | |

FOREIGN PATENT DOCUMENTS

| | | | |
|---|---|---|---|
| JP | H07-035940 | A | 2/1995 |
| JP | 2000-221326 | A | 8/2000 |
| JP | 2003-232963 | A | 8/2003 |
| JP | 2004-191914 | A | 7/2004 |
| JP | 3825930 | B2 | 9/2006 |

OTHER PUBLICATIONS

International Search Report dated Oct. 7, 2014 issued in PCT/JP2014/067578.
Chinese Office Action dated Apr. 1, 2017 in Chinese Patent Application No. 201480047841.6.
Extended Supplementary European Search Report dated Mar. 9, 2017 in European Patent Application No. 14 84 0297.7.

* cited by examiner

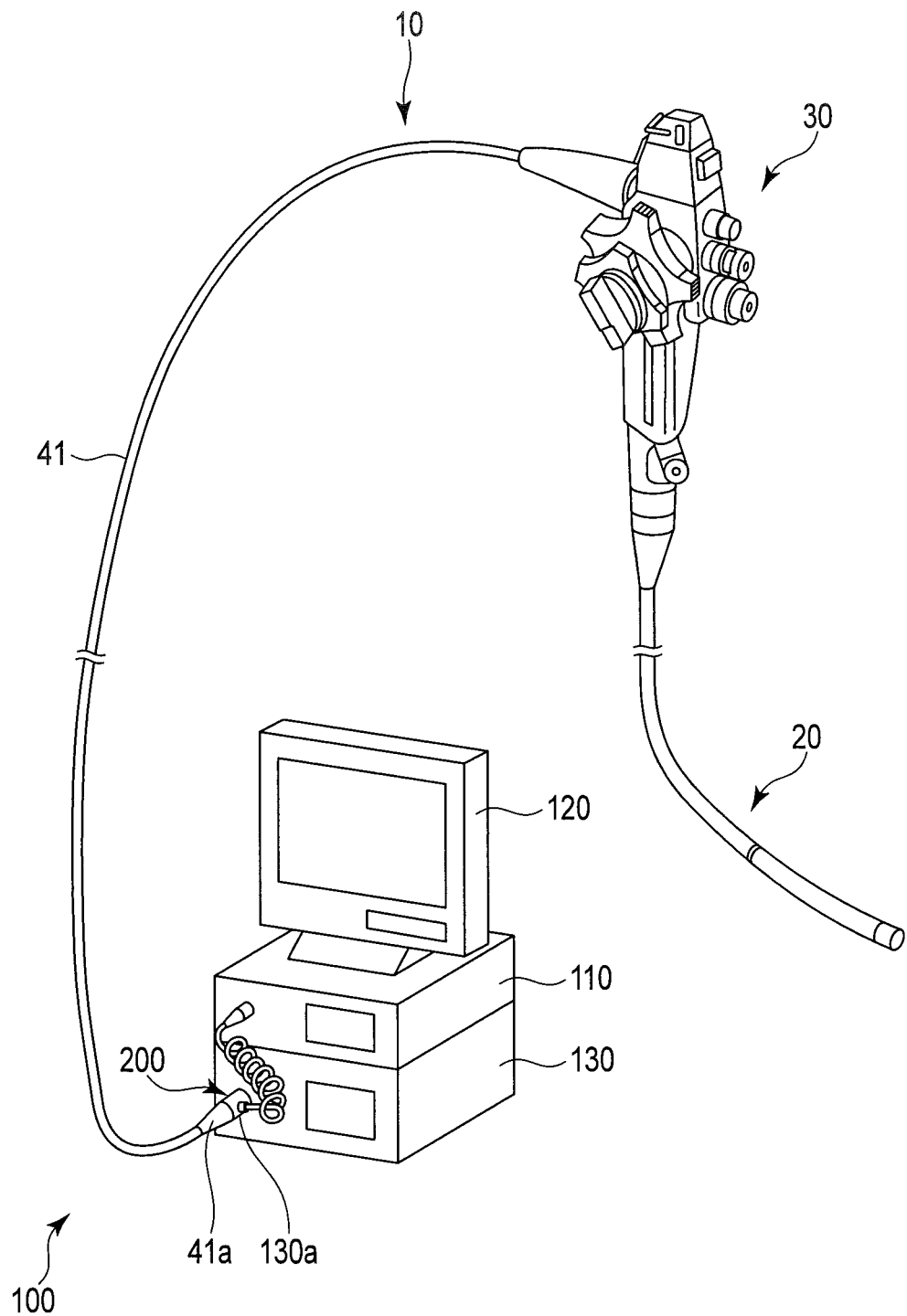
F I G. 1

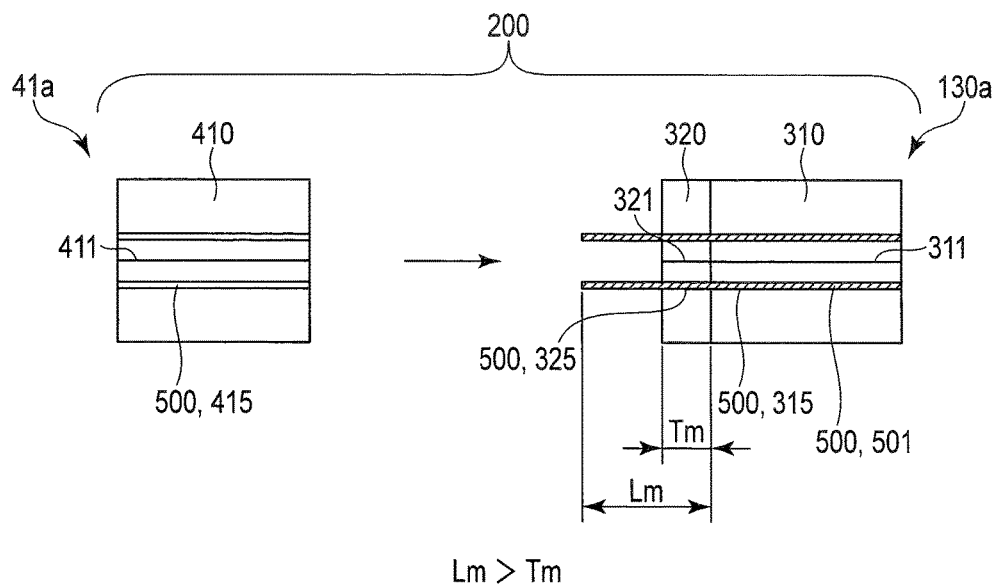
F I G. 4A
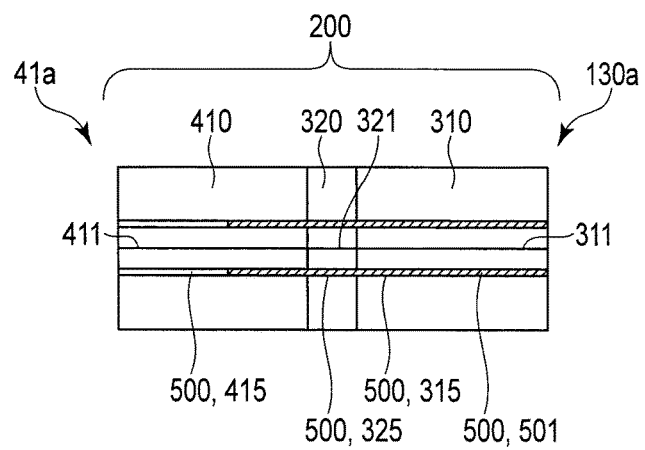
F I G. 4B

Lm > Tf

OPTICAL CONNECTOR FOR ENDOSCOPE

CROSS-REFERENCE TO RELATED APPLICATIONS

This application is a Continuation Application of PCT Application No. PCT/JP2014/067578, filed Jul. 1, 2014 and based upon and claiming the benefit of priority from prior Japanese Patent Application No. 2013-178688, filed Aug. 29, 2013, the entire contents of all of which are incorporated herein by reference.

BACKGROUND OF THE INVENTION

1. Field of the Invention

The present invention relates to an optical connector for an endoscope which optically couples a first waveguide provided in a connector of the endoscope to a second waveguide provided in a plug of a light source device to which the connector is connected.

2. Description of the Related Art

An optical connector which optically couples optical fibers to each other is disclosed in, for example, Japanese Patent No. 3825930. This optical connector is a single-core connector type. In the optical connector, the ends of the optical fibers are exposed in a normal state, and the ends can be replaced when the ends are damaged.

Each optical connector has an original ferrule of a body portion holding one optical fiber, and a replacement ferrule holding the other optical fiber. The body portion has a spring which presses the original ferrule. The optical connectors are optically connected to each other by an adaptor holding a sleeve therein.

When one optical connector is disconnected from the other optical connector, a flange of the replacement ferrule bumps into the exterior of one optical connector, and the original ferrule is pressed to the replacement ferrule by the spring. As a result, a press force is applied to the original ferrule and the replacement ferrule to press each other, and a press force is applied to an end face of one optical fiber and an end face of the other optical fiber to press each other. This also holds true with the other optical connector side.

When one optical connector is connected to the other optical connector, the replacement ferrule of one optical connector bumps into the replacement ferrule of the other connector inside the sleeve. In this instance, in one optical connector, the original ferrule is provided coaxially with the replacement ferrule. The original ferrule is then pressed to the replacement ferrule by the spring. As a result, a press force is applied to the original ferrule and the replacement ferrule to press each other, and a press force is applied to the end face of one optical fiber and the end face of the other optical fiber to press each other. This also holds true with the other connector side. In one optical fiber and the other optical fiber, the replacement ferrules press each other by the spring via the original ferrule. Therefore, the optical fiber in one replacement ferrule and the optical fiber in the other replacement ferrule are directly optically coupled to each other.

According to the configuration described above, a press force is always maintained between the original ferrule and the replacement ferrule during the shift from the disconnection state to the connection state of one optical fiber and the other optical fiber.

BRIEF SUMMARY OF THE INVENTION

According to an aspect of the present invention, an optical connector for an endoscope includes: a first holding member which holds a first waveguide therein, a second holding member which holds a second waveguide therein, a replaceable replacement member which has a replacement waveguide that is optically coupled to the first waveguide and the second waveguide and which intervenes between the first holding member and the second holding member so that the replacement waveguide intervenes between the first waveguide and the second waveguide and is optically coupled to the first waveguide and the second waveguide, an attachment member which presses the replacement member toward the side to which the replacement member is attached so that the replacement member is attached to at least one of the first holding member and the second holding member, and a positioning mechanism which positions the first holding member, the second holding member, and the replacement member relative to one another so that the replacement waveguide is optically coupled to the first waveguide and the second waveguide.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view of an endoscopic device equipped with an optical connector according to a first embodiment of the present invention;

FIG. 4A is a diagram showing a second modification of the optical connector, showing the relation between the lengths Tm and Lm, and showing how a first replacement waveguide is optically uncoupled from a second waveguide in a state where a first waveguide is optically coupled to the first replacement waveguide and;

FIG. 4B is a diagram showing how the first replacement waveguide is optically coupled to the second waveguide from the state shown in FIG. 4A;

DETAILED DESCRIPTION OF THE INVENTION

Figure 2A:
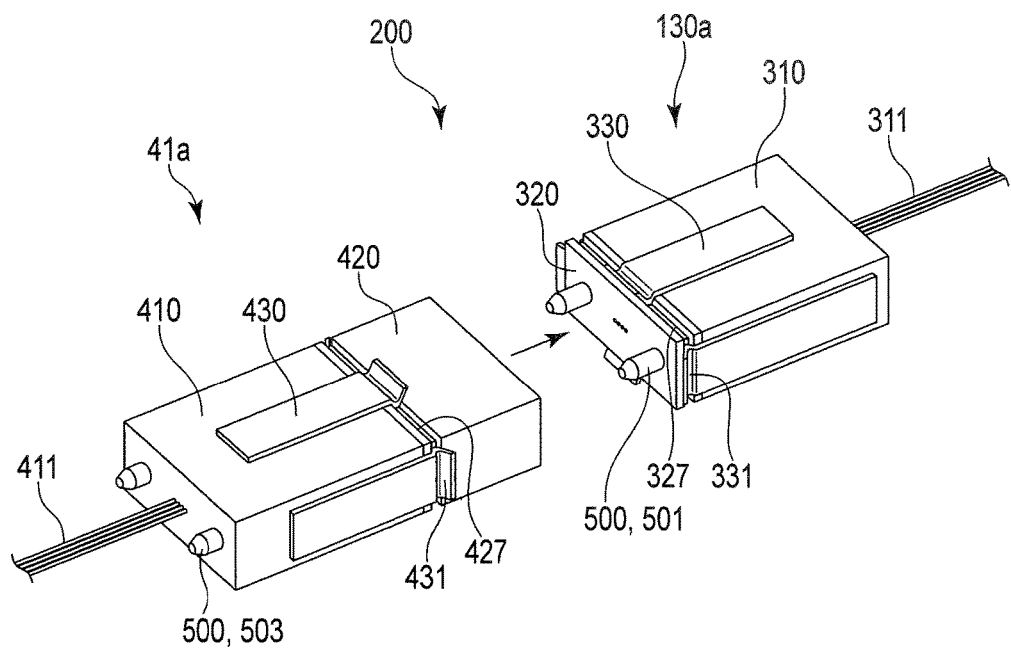
FIG. 2A is a perspective view of the optical connector.

Hereinafter, embodiments of the present invention will be described in detail with reference to the drawings.

First Embodiment

Configuration

The first embodiment is described with reference to FIG. 1, FIG. 2A, FIG. 2B, FIG. 2C, and FIG. 2D. Some components are omitted from some of the drawings for simplification of the drawings; for example, first attachment member 330 is omitted from FIG. 2C.

[Endoscopic Device 100]

An endoscopic device 100 shown in FIG. 1 is provided in, for example, an examination room or an operating room. As shown in FIG. 1, the endoscopic device 100 has an endoscope 10 which images the inside of a body cavity (lumen) of, for example, a patient, and an image processing device 110 (e.g., a video processor) which processes an image of the inside of the body cavity of, for example, the patient imaged by the endoscope 10. The endoscopic device 100 also has a display unit 120 which is connected to the image processing device 110 and which displays an image of the inside of the body cavity of, for example, the patient imaged by the endoscope 10 and processed by the image processing device 110, and a light source device 130 which emits light for illumination light emitted from the endoscope 10.

The endoscope 10 has a hollow and elongated insertion portion 20 to be inserted to a lumen such as a body cavity, an operation portion 30 which is coupled to a proximal end portion of the insertion portion 20 and which operates the endoscope 10, and a universal cord 41 which is connected to the operation portion 30 and which extends from the side surface of the operation portion 30.

The universal cord 41 has a connector 41a which is removably attachable to the image processing device 110 and the light source device 130. The connector 41a is connected the endoscope 10 and various devices (the image processing device 110 and the light source device 130), and is provided so that data are sent and received between these devices.

The connector 41a has an unshown electric connection portion provided to control an imaging unit provided at a distal end portion of the insertion portion 20, an unshown air/water supply connection portion provided to supply air/water, and a part of an optical connector for the endoscope provided for the light emitted from the light source device 130.

The image processing device 110 functions as a control device which controls the whole endoscopic device 100 including the endoscope 10, the display unit 120, and the light source device 130.

The image processing device 110 and the light source device 130 are electrically connected to each other. The image processing device 110 and the light source device 130 are removably connected to the endoscope 10 via the connector 41a.

[Optical Connector for Endoscope (Hereinafter, Optical Connector 200)]

The optical connector 200 shown in FIG. 2A is incorporated in a plug 130a (see FIG. 1) of the light source device 130 into which the connector 41a is plugged, and in the connector 41a.

Figure 2B:
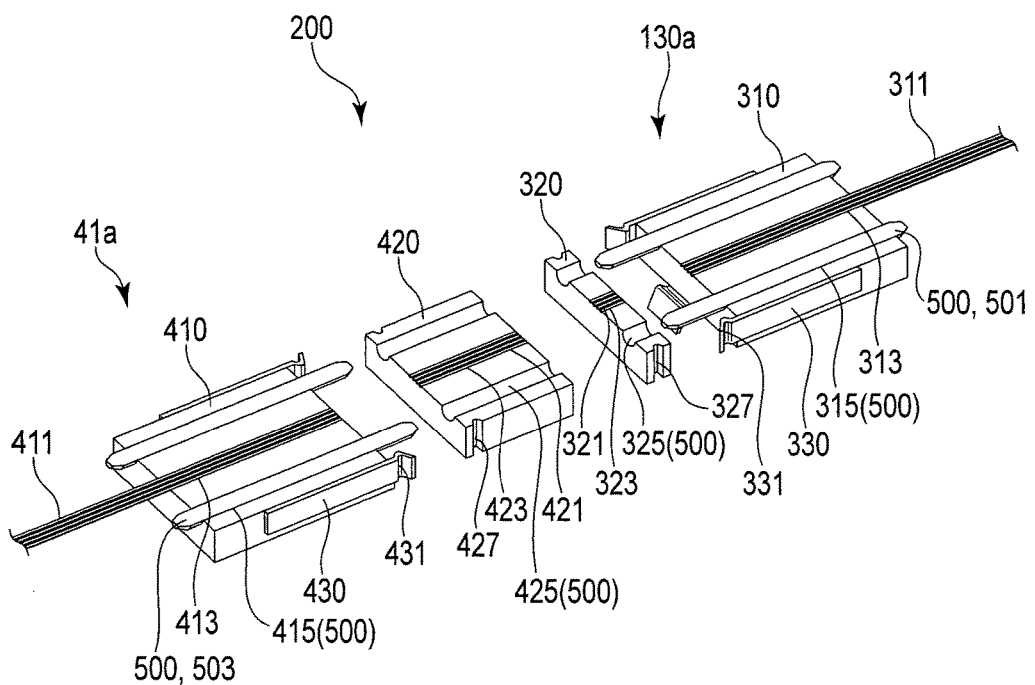
FIG. 2B is an exploded sectional perspective view of the optical connector shown in FIG. 2A.
Figure 2C:
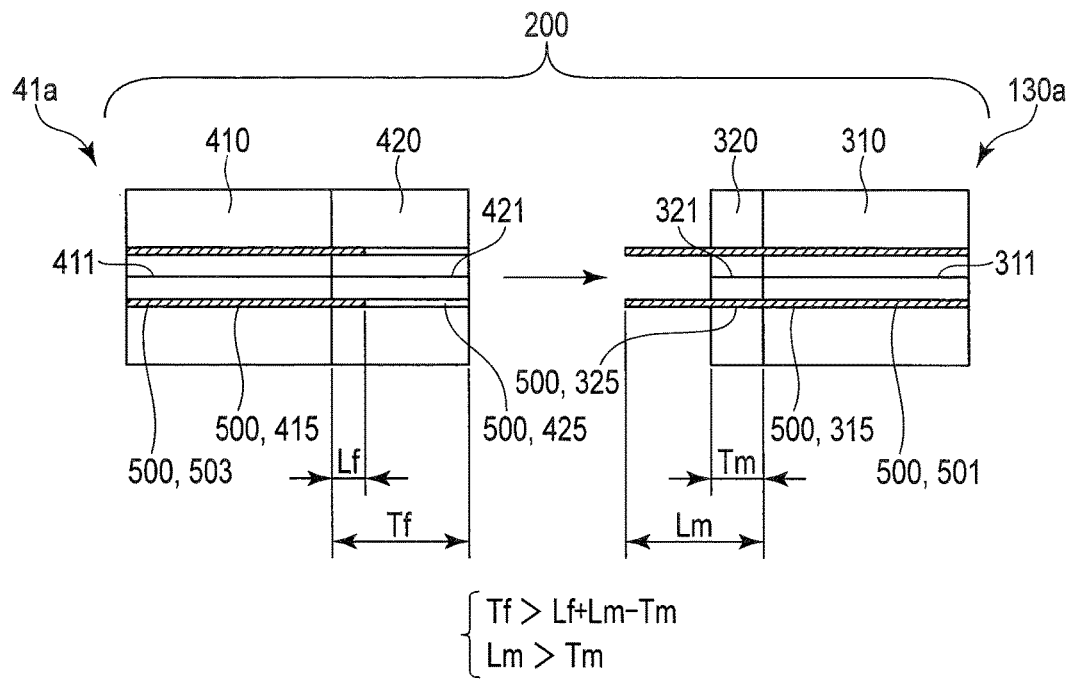
FIG. 2C is a diagram showing the relation between lengths Tm, Lm, Tf, and Lf, and showing how a first replacement waveguide is optically uncoupled from a second replacement waveguide in a state where a first waveguide is optically coupled to the first replacement waveguide.

As shown in FIG. 2A, FIG. 2B, and FIG. 2C, the optical connector 200 has a first holding member 310 which holds a first waveguide 311 therein, and a first replacement member 320 which can replace the first holding member 310. The optical connector 200 also has the first attachment member 330 which presses, for example, the first replacement member 320 to the first holding member 310, thereby attaches the first replacement member 320 to the first holding member 310.

As shown in FIG. 2A, FIG. 2B, and FIG. 2C, the optical connector 200 also has a second holding member 410 which holds a second waveguide 411 therein, and a second replacement member 420 which can replace the second holding member 410. The optical connector 200 also has a second attachment member 430 which presses, for example, the second replacement member 420 to the second holding member 410, thereby attach the second replacement member 420 to the second holding member 410.

As shown in FIG. 2A, FIG. 2B, FIG. 2C, and FIG. 2D, the optical connector 200 also has a positioning mechanism 500 which positions the first holding member 310, the second holding member 410, the first replacement member 320, and the second replacement member 420 relative to one another so that the first waveguide 311 is optically coupled to a first replacement waveguide 321 of the first replacement member 320, so that the second waveguide 411 is optically coupled to a second replacement waveguide 421 of the second replacement member 420, and so that the first replacement waveguide 321 is optically coupled to the second replacement waveguide 421.

The first holding member 310 side including the first replacement member 320 and the first attachment member 330 is, for example, a projecting type, and is incorporated in the plug 130a of the light source device 130 into which the connector 41a is plugged.

The second holding member 410 side including the second replacement member 420 and the second attachment member 430 is, for example, a depressed type, and is incorporated in the connector 41a which is plugged into the plug 130a.

The first waveguide 311, the second waveguide 411, the first replacement waveguide 321, and the second replacement waveguide 421 have only to be equal in number. The first waveguide 311 has, for example, at least one optical fiber. This also holds true for the second waveguide 411, the first replacement waveguide 321, and the second replacement waveguide 421. There may be more than one of each of these waveguides. When the first waveguide 311, the second waveguide 411, the first replacement waveguide 321, and the second replacement waveguide 421 have optical fibers, the optical fibers may be single-cored or multi-cored.

[First Holding Member 310]

The first holding member 310 has a ferrule formed by, for example, resin molding.

As shown in FIG. 2B, the first holding member 310 has an insertion slot portion 313 to which the first waveguide 311 is inserted, and an insertion slot portion 315 into which a later-described first positioning member 501 of the positioning mechanism 500 is inserted.

As shown in FIG. 2B, the insertion slot portion 313 is provided along the longitudinal axis direction of the first holding member 310, and passes through the first holding member 310 in the longitudinal axis direction. The first waveguide 311 is inserted to the insertion slot portion 313 and then, for example, adhesively fixed to the insertion slot portion 313, whereby the first holding member 310 holds the first waveguide 311. This insertion slot portion 313 is provided, for example, in the center of the first holding member 310.

As shown in FIG. 2B, an end face of the first holding member 310 can be, for example, polished together with an end face of the first waveguide 311 while the first holding member 310 is holding the first waveguide 311 so that the end face of the first holding member 310 is provided flush with the end face of the first waveguide 311 and so that the end face of the first holding member 310 and the end face of the first waveguide 311 are smoothed. This end face is, for example, a surface on the side where the first replacement member 320 is attached.

As shown in FIG. 2B, the insertion slot portion 315 is provided along the longitudinal axis direction of the first holding member 310, and passes through the first holding member 310 in the longitudinal axis direction. For example, the insertion slot portions 315 are provided on both sides of the insertion slot portion 313. For example, only two insertion slot portions 315 may be provided point-symmetrically with respect to the first waveguide 311 as a center. When the first holding member 310 is formed by resin molding, the insertion slot portion 315 is formed simultaneously with the insertion slot portion 313 so that the insertion slot portion 315 is positioned relative to the insertion slot portion 313.

[First Replacement Member 320]

As shown in FIG. 2A and FIG. 2B, the configuration of the first replacement member 320 is substantially the same as the configuration of the first holding member 310, and is therefore not described in detail. The waveguide corresponding to the first waveguide 311 is referred to as the first replacement waveguide 321, the insertion slot portion corresponding to the insertion slot portion 313 is referred to as a replacement insertion slot portion 323, and the insertion slot portion corresponding to the insertion slot portion 315 is referred to as a replacement insertion slot portion 325. The first replacement member 320 holds therein the first replacement waveguide 321 which is optically coupled to the first waveguide 311. The same number of first replacement waveguides 321 as the first waveguides 311 are provided, the same number of replacement insertion slot portions 323 as the insertion slot portions 313 are provided, and the same number of replacement insertion slot portions 325 as the insertion slot portions 315 are provided.

When the first replacement member 320 is formed by resin molding, the replacement insertion slot portion 325 is formed simultaneously with the replacement insertion slot portion 323 so that the replacement insertion slot portion 325 is positioned relative to the replacement insertion slot portion 323.

The replacement insertion slot portion 323 is formed to be positioned relative to the insertion slot portion 313. The replacement insertion slot portion 325 is formed to be positioned relative to the insertion slot portion 315.

The first replacement member 320 is preferably formed in a process different from that of the first holding member 310 in consideration of the replaceablity of the first replacement member 320. It should be understood that the first replacement member 320 and the first holding member 310 may be formed as one unit and then separated.

As shown in FIG. 2A and FIG. 2B, regarding a sectional area A1 of the first holding member 310 and a sectional area A2 of the first replacement member 320, the shape of the sectional area A1 is the same as the shape of the sectional area A2, and the size of the sectional area A1 is the same as the size of the sectional area A2. The sectional area A1 is a surface of the first holding member 310 cut perpendicularly to the longitudinal axis of the first holding member 310. The sectional area A2 is a surface of the first replacement member 320 cut perpendicularly to the central axis of the first replacement member 320 provided coaxially with the longitudinal axis of the first holding member 310.

Similarly to the end face of the first holding member 310, an end face of the first replacement member 320 can be, for example, polished together with an end face of the first replacement waveguide 321 while the first replacement member 320 is holding the first replacement waveguide 321 so that the end face of the first replacement member 320 is provided flush with the end face of the first replacement waveguide 321 and so that the end face of the first replacement member 320 and the end face of the first replacement waveguide 321 are smoothed. This polishing is possible on both end faces of the first replacement member 320 in the axial direction of the optical connector 200. These end faces have an end face which abuts on the end face of the first holding member 310 and an end face which abuts on an end face of the second replacement member 420.

As shown in FIG. 2A and FIG. 2B, the first replacement member 320 is attached to the first holding member 310 so that the smooth end face of the first replacement member 320 comes into abutment with and into close contact with the smooth end face of the first holding member 310, so that the first waveguide 311 is provided in alignment with the first replacement waveguide 321 in the axial direction of the optical connector 200, so that the first waveguide 311 is optically coupled to the first replacement waveguide 321, and so that the insertion slot portion 315 communicates with the replacement insertion slot portion 325 in the axial direction of the optical connector 200.

The first replacement member 320 attached to the first holding member 310 intervenes between the second replacement member 420 and the first holding member 310 in the axial direction of the optical connector 200.

As shown in FIG. 2A, FIG. 2B, FIG. 2C, and FIG. 2D, the length of the first replacement member 320 is different from the length of the second replacement member 420, and is smaller than the length of the second replacement member 420 in the present embodiment.

The difference between the configuration of the first replacement member 320 and the configuration of the first holding member 310 is as below.

As shown in FIG. 2A and FIG. 2B, the first replacement member 320 has a first catching portion 327 which is formed in a circumferential surface of the first replacement member 320 and on which a distal end portion of the first attachment member 330 is caught. The first catching portion 327 is provided point-symmetrically with respect to the first replacement waveguide 321 as a center. The first catching portion 327 has, for example, a first groove portion formed over the entire side surface of the first replacement member 320. The first groove portion has, for example, a depressed section. The first groove portion is, for example, depressed perpendicularly to the side surface of the first replacement member 320.

[First Attachment Member 330]

As shown in FIG. 2A and FIG. 2B, the first attachment member 330 is provided in the first holding member 310 as an attachment side to which the first replacement member 320 is attached so that the first attachment member 330 is provided point-symmetrically with respect to the first waveguide 311 as a center provided in the first holding member 310 which is the attachment side. The first attachment member 330 has only to be provided point-symmetrically with respect to the first waveguide 311 as a center. The first attachment member 330 may be provided around the first waveguide 311 in such a manner as to surround the first waveguide 311 from all directions. The first attachment member 330 has a proximal end portion fixed by, for example, adhesive bonding to each circumferential surface of the first holding member 310 as the side to which the first replacement member 320 is attached.

The first attachment member 330 presses the first replacement member 320 toward the first holding member 310 which is the attachment side so that the first replacement member 320 is attached to the first holding member 310. Thus, as shown in FIG. 2A and FIG. 2B, the first attachment member 330 has a first claw portion 331 which is provided at the distal end portion of the first attachment member 330 and which is caught on the first catching portion 327 of the first replacement member 320. The first claw portion 331 has a press force which presses the first replacement member 320 toward the first holding member 310 which is a side to which the first replacement member 320 is attached when the first claw portion 331 is caught on the first catching portion 327 so that the first replacement member 320 is attached to the first holding member 310 as described above. The press force is exerted in the axial direction of the optical connector 200. The first claw portion 331 brings the end face of the first holding member 310 including the first waveguide 311 into close contact with the end face of the first replacement member 320 including the first replacement waveguide 321 by the press force, and maintains a sealing state in these end faces.

As shown in FIG. 2A and FIG. 2B, the first claw portion 331 has, for example, a leaf spring portion. The first claw portion 331 has a portion which is bent to be caught on the first catching portion 327. This portion is, for example, formed to bulge in a direction that intersects at right angles with the axial direction of the axial direction of the first attachment member 330.

[Second Holding Member 410]

As shown in FIG. 2A and FIG. 2B, the configuration of the second holding member 410 is substantially the same as the configuration of the first holding member 310, and is therefore not described in detail. The insertion slot portion corresponding to the insertion slot portion 313 is referred to as an insertion slot portion 413, and the insertion slot portion corresponding to the insertion slot portion 315 is referred to as an insertion slot portion 415.

[Second Replacement Member 420]

As shown in FIG. 2A and FIG. 2B, the configuration of the second replacement member 420 is substantially the same as the configuration of the first replacement member 320, and is therefore not described in detail. The replacement waveguide corresponding to the first replacement waveguide 321 is referred to as the second replacement waveguide 421, the replacement insertion slot portion corresponding to the replacement insertion slot portion 323 is referred to as a replacement insertion slot portion 423, the replacement insertion slot portion corresponding to the replacement insertion slot portion 325 is referred to as a replacement insertion slot portion 425, the catching portion corresponding to the first catching portion 327 is referred to as a second catching portion 427, and the groove portion corresponding to the first groove portion is referred to as a second groove portion.

When the second replacement member 420 is formed by resin molding, the replacement insertion slot portion 425 is formed simultaneously with the replacement insertion slot portion 423 so that the replacement insertion slot portion 425 is positioned relative to the replacement insertion slot portion 423.

The replacement insertion slot portion 423 is formed to be positioned relative to the insertion slot portion 413. The replacement insertion slot portion 425 is formed to be positioned relative to the insertion slot portion 415.

The second replacement member 420 is preferably formed in a process different from that of the second holding member 410 in consideration of the replaceablity of the second replacement member 420. It should be understood that the second replacement member 420 and the second holding member 410 may be formed as one unit and then separated.

As shown in FIG. 2A and FIG. 2B, regarding a sectional area B1 of the second holding member 410 and a sectional area B2 of the second replacement member 420, the shape of the sectional area B1 is the same as the shape of the sectional area B2, and the size of the sectional area B1 is the same as the size of the sectional area B2. The shape of sectional area B1 is the same as the shape of the sectional area A1, and the size of the sectional area B1 is the same as the size of the sectional area A1. The sectional area B1 is a surface of the second holding member 410 cut perpendicularly to the longitudinal axis of the second holding member 410. The sectional area B2 is a surface of the second replacement member 420 cut perpendicularly to the central axis of the second replacement member 420 provided coaxially with the longitudinal axis of the second holding member 410.

Similarly to an end face of the second holding member 410, the end face of the second replacement member 420 can be, for example, polished together with an end face of the second replacement waveguide 421 while the second replacement member 420 is holding the second replacement waveguide 421 so that the end face of the second replacement member 420 is provided flush with the end face of the second replacement waveguide 421 and so that the end face of the second replacement member 420 and the end face of the second replacement waveguide 421 are smoothed. This polishing is possible on both end faces of the second replacement member 420 in the axial direction of the optical connector 200. These end faces have an end face which abuts on the end face of the second holding member 410 and an end face which abuts on the end face of the first replacement member 320.

As shown in FIG. 2A and FIG. 2B, the second replacement member 420 is attached to the second holding member 410 so that the smooth end face of the second replacement member 420 comes into abutment with and into close contact with the smooth end face of the second holding member 410, so that the second waveguide 411 is provided in alignment with the second replacement waveguide 421 in the axial direction of the optical connector 200, so that the second waveguide 411 is optically coupled to the second replacement waveguide 421, and so that the insertion slot portion 415 communicates with the replacement insertion slot portion 425 in the axial direction of the optical connector 200.

The second replacement member 420 attached to the second holding member 410 intervenes between the first replacement member 320 and the second holding member 410 in the axial direction of the optical connector 200.

The relative positions of the second holding member 410 and the second replacement member 420 are substantially the same as the relative positions of the first holding member 310 and the first replacement member 320.

[Second Attachment Member 430]

As shown in FIG. 2A and FIG. 2B, the configuration of the second attachment member 430 is substantially the same as the configuration of the first attachment member 330, and is therefore not described in detail. The claw portion corresponding to the first claw portion 331 is referred to as a second first claw portion 431. The second attachment member 430 is provided in the second holding member 410 in the same manner that the first attachment member 330 is provided in the first holding member 310. The second attachment member 430 causes the second holding member 410 to perform a function substantially similar to that of the first attachment member 330 substantially in a similar manner as the function of the first attachment member 330 on the first holding member 310.

[Positioning Mechanism 500]

As shown in FIG. 2A, FIG. 2B, FIG. 2C, and FIG. 2D, the positioning mechanism 500 has the insertion slot portion 315 which is a first holding side insertion slot portion, and the replacement insertion slot portion 325 which is a first replacement side insertion slot portion. The positioning mechanism 500 also has the insertion slot portion 415 which is a second holding side insertion slot portion, and the replacement insertion slot portion 425 which is a second replacement side insertion slot portion. The positioning mechanism 500 also has the first positioning member 501 which engages with the insertion slot portion 315, the replacement insertion slot portion 325, and the replacement insertion slot portion 425, and a second positioning member 503 which engages with the insertion slot portion 415 and the replacement insertion slot portion 425. The first positioning member 501 has, for example, a pin. The second positioning member 503 has, for example, a pin.

As shown in FIG. 2C, the first positioning member 501 engages with the insertion slot portion 315 and the replacement insertion slot portion 325 so that a distal end portion of the first positioning member 501 which functions as a protrusion portion passes through the replacement insertion slot portion 325 via the insertion slot portion 315 when the first replacement waveguide 321 is optically uncoupled from the second replacement waveguide 421 while the first waveguide 311 is optically coupled to the first replacement waveguide 321. The above optical uncoupling shows the state of not being optically coupled. The optical uncoupling shows, for example, that the first replacement waveguide 321 is provided away from the second replacement waveguide 421.

Figure 2D:
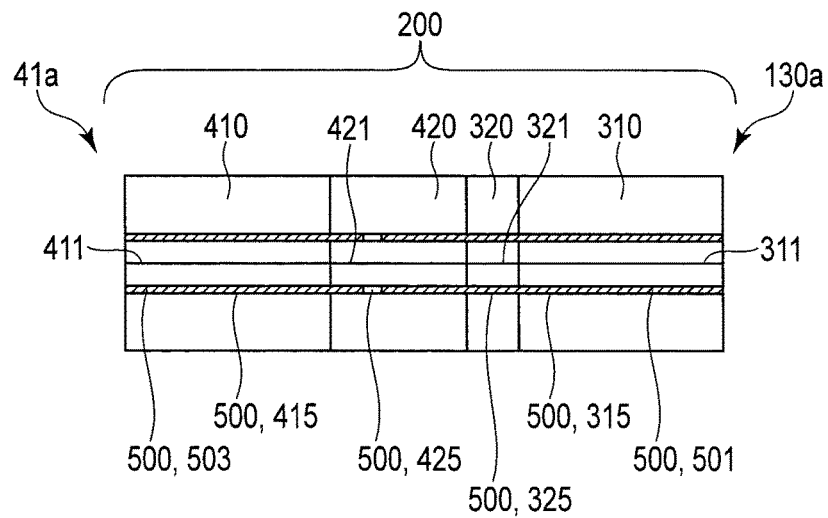
FIG. 2D is a diagram showing how the first replacement waveguide is optically coupled to the second replacement waveguide from the state shown in FIG. 2C.

As shown in FIG. 2D, the first positioning member 501 engages with the insertion slot portion 315, the replacement insertion slot portion 325, and the replacement insertion slot portion 425 so that the distal end portion which passes through the replacement insertion slot portion 325 is inserted to the replacement insertion slot portion 425 when the first replacement waveguide 321 is optically coupled to the second replacement waveguide 421 while the first waveguide 311 is optically coupled to the first replacement waveguide 321.

As shown in FIG. 2C and FIG. 2D, the second positioning member 503 engages with the insertion slot portion 415 and the replacement insertion slot portion 425 so that the second waveguide 411 is optically coupled to the second replacement waveguide 421.

Here, as shown in FIG. 2C, the length of the replacement insertion slot portion 325 is referred to as Tm, the length of the distal end portion of the first positioning member 501 which functions as the protrusion portion protruding from the insertion slot portion 315 is referred to as Lm, the length of the replacement insertion slot portion 425 is referred to as Tf, and the length of a protrusion portion of the second positioning member 503 protruding from the insertion slot portion 415 is referred to as Lf.

As shown in FIG. 2C and FIG. 2D, when the positioning mechanism 500 positions the first holding member 310, the second holding member 410, the first replacement member 320, and the second replacement member 420 relative to one another, Equations (1), (2), (3), and (4) below are satisfied in the present embodiment.

$$Tf > Lf + Lm - Tm \qquad \text{Equation (1)}$$

$$Lm > Tm \qquad \text{Equation (2)}$$

$$Tf > Lf \qquad \text{Equation (3)}$$

$$Tf > Tm \qquad \text{Equation (4)}$$

As shown in FIG. 2C, the first positioning member 501 is inserted to and engages with the insertion slot portion 315 and the replacement insertion slot portion 325. Thus, the first positioning member 501 positions the first holding member 310 and the first replacement member 320 so that the first waveguide 311 is optically coupled to the first replacement waveguide 321. In this instance, the distal end portion of the first positioning member 501 protrudes outward from the replacement insertion slot portion 325 in accordance with the above equations.

As shown in FIG. 2C, the second positioning member 503 is inserted to and engages with the insertion slot portion 415 and the replacement insertion slot portion 425. Thus, the second positioning member 503 positions the second holding member 410 and the second replacement member 420 so that the second waveguide 411 is optically coupled to the second replacement waveguide 421.

As shown in FIG. 2D, the distal end portion of the first positioning member 501 is inserted to and engages with the replacement insertion slot portion 425. Thus, the distal end portion of the first positioning member 501 positions, relative to each other, the first holding member 310 to which the first replacement member 320 is attached and the second holding member 410 to which the second replacement member 420 is attached so that the first replacement waveguide 321 optically coupled to the first waveguide 311 is optically coupled to the second replacement waveguide 421 optically coupled to the second waveguide 411.

[Functions]

[Assembly of First Holding Member 310 Side]

As shown in FIG. 2B, in the first holding member 310, the first waveguide 311 is inserted to the insertion slot portion 313, and, for example, adhesively fixed to the insertion slot portion 313. Thus, the first holding member 310 holds the first waveguide 311.

In the above state, the end face of the first holding member 310 is polished together with the end face of the first waveguide 311. This end face represents a surface on the side where the first replacement member 320 is attached. Thus, the end face of the first holding member 310 is provided flush with the end face of the first waveguide 311, and the end face of the first holding member 310 and the end face of the first waveguide 311 are smoothed.

As shown in FIG. 2B, in the first replacement member 320, the first replacement waveguide 321 is inserted to the replacement insertion slot portion 323, and, for example, adhesively fixed to the replacement insertion slot portion 323. Thus, the first replacement member 320 holds the first replacement waveguide 321.

In the above state, the end face of the first replacement member 320 is polished together with the end face of the first replacement waveguide 321. This end face represents both end faces of the first replacement member 320 in the axial direction of the optical connector 200, the end face facing the polished end face of the first holding member 310, and the end face facing the polished end face of the second holding member 410. Thus, the end face of the first replacement member 320 is provided flush with the end face of the first replacement waveguide 321, and the end face of the first replacement member 320 and the end face of the first replacement waveguide 321 are smoothed.

As shown in FIG. 2A and FIG. 2C, the first attachment member 330 attaches the first replacement member 320 to the first holding member 310 so that the smooth end face of the first replacement member 320 comes into abutment with and into close contact with the smooth end face of the first holding member 310, so that the first waveguide 311 is provided in alignment with the first replacement waveguide 321 in the axial direction of the optical connector 200, so that the first waveguide 311 is optically coupled to the first replacement waveguide 321, and so that the insertion slot portion 315 communicates with the replacement insertion slot portion 325 in the axial direction of the optical connector 200. In this instance, the first claw portion 331 is caught on the first catching portion 327, and presses the first replacement member 320 toward the first holding member 310. Thus, the end face of the first holding member 310 including the first waveguide 311 comes into close contact with the end face of the first replacement member 320 including the first replacement waveguide 321, so that the sealing state is maintained.

As described above, regarding the sectional area A1 of the first holding member 310 and the sectional area A2 of the first replacement member 320, the shape of the sectional area A1 is the same as the shape of the sectional area A2, and the size of the sectional area A1 is the same as the size of the sectional area A2. The replacement insertion slot portion 323 is formed to be positioned relative to the insertion slot portion 313. Thus, the first waveguide 311 can be provided in alignment with the first replacement waveguide 321 in the axial direction of the optical connector 200. The first waveguide 311 can be optically coupled to the first replacement waveguide 321.

Thus, the first replacement member 320 is attached to the first holding member 310, and the first replacement waveguide 321 is optically coupled to the first waveguide 311.

As shown in FIG. 2A, FIG. 2B, and FIG. 2C, the first positioning member 501 is inserted from the insertion slot portion 315 toward the replacement insertion slot portion 325. The first positioning member 501 engages with the insertion slot portion 315 and the replacement insertion slot portion 325 so that the distal end portion of the first positioning member 501 which functions as the protrusion portion passes through the replacement insertion slot portion 325 via the insertion slot portion 315. Thus, the distal end portion of the first positioning member 501 which functions as the protrusion portion passes through the replacement insertion slot portion 325 toward the second holding member 410 side, and is exposed to the outside from the first replacement member 320.

In this case, as described above, the first replacement member 320 is attached to the first holding member 310, the first waveguide 311 is optically coupled to the first replacement waveguide 321, the first replacement member 320 is not attached to the second replacement member 420, and the first replacement waveguide 321 is optically uncoupled from the second replacement waveguide 421.

The first attachment member 330 and the first positioning member 501 may be provided in reverse order.

In this way, the first holding member 310 side is assembled. The assembled first holding member 310 side is incorporated in the plug 130a of the light source device 130.

[Assembly of Second Holding Member 410 Side]

The second holding member 410 is substantially similar to the first holding member 310 described above.

The second replacement member 420 is substantially similar to the first replacement member 320 described above.

The second attachment member 430 is substantially similar to the first attachment member 330 described above.

By the second attachment member 430, the second replacement member 420 is attached to the second holding member 410, and the second replacement waveguide 421 is optically coupled to the second waveguide 411.

As shown in FIG. 2A, FIG. 2B, and FIG. 2C, the second positioning member 503 is inserted from the insertion slot portion 415 toward the replacement insertion slot portion 425. The second positioning member 503 engages with the insertion slot portion 415 and the replacement insertion slot portion 425 so that the second replacement waveguide 421 is optically coupled to the second waveguide 411. The distal end portion of the second positioning member 503 does not pass through the replacement insertion slot portion 425, and is located inside the replacement insertion slot portion 425. In this case, as described above, the second replacement member 420 is attached to the second holding member 410, the second waveguide 411 is optically coupled to the second replacement waveguide 421, the first replacement member 320 is not attached to the second replacement member 420, and the first replacement waveguide 321 is optically uncoupled from the second replacement waveguide 421.

The second attachment member 430 and the second positioning member 503 may be provided in reverse order.

In this way, the second holding member 410 side is assembled. The assembled second holding member 410 side is incorporated in the connector 41a.

[Connection Work of First Holding Member 310 Side and Second Holding Member 410 Side]

In the present embodiment, as shown in FIG. 2C and FIG. 2D, Equations (1) and (2) below are satisfied.

$$Tf > Lf + Lm - Tm \quad \text{Equation (1)}$$

$$Lm > Tm \quad \text{Equation (2)}$$

Therefore, as shown in FIG. 2C and FIG. 2D, the connector 41a is plugged into the plug 130a, whereby the distal end portion of the first positioning member 501 which is exposed to the outside through the replacement insertion slot portion 325 is inserted to the replacement insertion slot portion 425 and engages with the replacement insertion slot portion 425. As a result, the distal end portion of the first positioning member 501 positions, relative to each other, the first holding member 310 to which the first replacement member 320 is attached and the second holding member 410 to which the second replacement member 420 is attached so that the first replacement waveguide 321 optically coupled to the first waveguide 311 is optically coupled to the second replacement waveguide 421 optically coupled to the second waveguide 411. The first replacement member 320 is then connected to the second replacement member 420, and the first holding member 310 side is connected to the second holding member 410 side.

An unshown press mechanism presses the first holding member 310 toward the second holding member 410 and presses the second holding member 410 toward the first holding member 310 in the axial direction of the optical connector 200 so that the end face of the first replacement member 320 including the end face of the first replacement waveguide 321 comes into close contact with the end face of the second replacement member 420 including the second replacement waveguide 421 and so that the sealing state is maintained.

[Replacement Work]

After the use of the endoscope 10, the endoscope 10 needs to be sterilized, disinfected, and washed. Thus, the connector 41a is unplugged from the plug 130a, and the optical connector 200 is disconnected. When the endoscope 10 is used, the connector 41a is plugged into the plug 130a, and the optical connector 200 is connected, as described above.

In contrast with the present embodiment, suppose that the first replacement member 320 and the second replacement member 420 are not provided, and the first holding member 310 is directly connected to the second holding member 410 so that the first waveguide 311 is optically coupled to the second waveguide 411. In this case, if unplugging is performed and the optical connector 200 is disconnected, for example, in the first waveguide 311 and the second waveguide 411, the sealing state is temporarily cancelled, and foreign objects such as water and dirt enter the space between the first waveguide 311 and the second waveguide 411. As a result, there is concern over the deterioration of optical coupling efficiency. There is also a concern that the foreign objects that have entered may damage an optical coupling portion that functions as the end face of the first waveguide 311 and the end face of the second waveguide 411 and that the optical coupling efficiency may deteriorate.

That is, the entry of the foreign objects into the optical coupling portion attributed to the temporary cancelling of the sealing state directly causes the deterioration of the optical coupling efficiency, and indirectly causes the deterioration of the optical coupling efficiency due to damage caused to the optical coupling portion.

If the above unplugging and plugging are repeated, the optical connector 200 is switched from the disconnection state to the connection state, or the optical connector 200 is switched from the connection state to the disconnection state. In this case, there is a concern over damage to the end face of the first waveguide 311 which is an optical coupling portion, the end face of the first holding member 310 provided flush with this end face of the first waveguide 311, the end face of the second waveguide 411 which is an optical coupling portion, and the end face of the second holding member 410 provided flush with this end face of the second waveguide 411. There is also concern that the foreign objects may adhere to these end faces. The above can cause the deterioration of the optical coupling efficiency.

Ways to eliminate such deterioration of the optical coupling efficiency include cleaning the above end faces with an exclusive cleaner, and polishing the end faces. However, considering the fact that the first holding member 310 side is incorporated in the plug 130a and that the second holding member 410 side is incorporated in the connector 41a, it takes time to, for example, disassemble the light source device 130 having the plug 130a to take out the first holding member 310 side. Moreover, for example, the first positioning member 501 cause a blockage, and the above methods cannot be applied to the first holding member 310 side.

However, in the present embodiment, the first replacement member 320 and the second replacement member 420 are provided.

The first replacement member 320 is always attached to the first holding member 310 when the connector 41a is unplugged from the plug 130a and the optical connector 200 is disconnected, or when the connector 41a is plugged into the plug 130a and the optical connector 200 is connected, or when the above unplugging and plugging are repeated and the optical connector 200 is switched from the disconnection state to the connection state or the optical connector 200 is switched from the connection state to the disconnection state.

Thus, the sealing state is always maintained without being canceled for the first waveguide 311 and the first replacement waveguide 321. Therefore, the entry of foreign objects into the space between the first waveguide 311 and the first replacement waveguide 321 is prevented. Thus, the deterioration of the optical coupling efficiency is prevented. The optical coupling portion that function as the end face of the first waveguide 311 and the end face of the first replacement waveguide 321 is not damaged by the foreign objects, and the deterioration of the optical coupling efficiency is prevented.

Even if the above unplugging and plugging are repeated and the optical connector 200 is switched from the disconnection state to the connection state or the optical connector 200 is switched from the connection state to the disconnection state, the end face of the first waveguide 311 which is the optical coupling portion, the end face of the first holding member 310 provided flush with this end face of the first waveguide 311, the end face of the first replacement member 320 which is the optical coupling portion, and the end face of the first replacement waveguide 321 provided flush with this end face of the first replacement member 320 are not damaged. The adhesion of foreign objects such as water and dirt to these end faces is also prevented. Therefore, the deterioration of the optical coupling efficiency is prevented in the first holding member 310 and the first replacement member 320.

This also holds true with the second holding member 410 and the second replacement member 420.

If the connector 41a is unplugged from the plug 130a and the optical connector 200 is disconnected, the first replacement member 320 is disconnected from the second replacement member 420. In this case, for example, in the first replacement waveguide 321 and the second replacement waveguide 421, the sealing state is cancelled, and foreign objects enter the space between the first replacement waveguide 321 and the second replacement waveguide 421. As a result, there is concern over the deterioration of the optical coupling efficiency. There is also concern that the foreign objects that have entered may damage the optical coupling portion that function as the end face of the first replacement waveguide 321 and the end face of the second replacement waveguide 421 and that the optical coupling efficiency may deteriorate.

That is, the entry of the foreign objects into the optical coupling portion attributed to the temporary cancelling of the sealing state directly causes the deterioration of the optical coupling efficiency, and indirectly causes the deterioration of the optical coupling efficiency by damaging the optical coupling portion.

If the above unplugging and plugging are repeated and the optical connector 200 is switched from the disconnection state to the connection state or the optical connector 200 is switched from the connection state to the disconnection state, the end face of the first replacement waveguide 321 which is the optical coupling portion, the end face of the first replacement member 320 provided flush with this end face of the first replacement waveguide 321, the end face of the second replacement waveguide 421 which is the optical coupling portion, and the end face of the second replacement member 420 provided flush with this end face of the second replacement waveguide 421 may be damaged. There is also concern over the adhesion of the foreign objects to these end faces. These cause the deterioration of the optical coupling efficiency.

In the present embodiment, in this case, for example, an exclusive jig is used, and the first claw portion 331 which is caught on the first catching portion 327 is released from the first catching portion 327 by the jig. For example, the first replacement member 320 having the end face to which the foreign objects are adhering is then removed from the first holding member 310. The end face to which the foreign objects are adhering is cleaned with, for example, an exclusive cleaner so that the foreign objects will be removed. When the end face is damaged, the end face is polished to be smooth. A new first replacement member 320 may be attached to the first holding member 310.

This also holds true with the second replacement member 420.

According to the contents described above, the fact that the first holding member 310 side is incorporated in the plug 130a and that the second holding member 410 side is incorporated in the connector 41a mean that it is not necessary to, for example, disassemble the light source device 130 having the plug 130a, and it saves time and labor in order to take out the first holding member 310 side. Moreover, for example, the first positioning member 501 does not cause a blockage, and the above methods can be applied.

According to the above, in the present embodiment, when the end face of the first replacement waveguide 321 and the end face of the second replacement waveguide 421 which are the optical coupling portions are damaged by foreign objects, the optical coupling portion can be easily replaced. Moreover, in the present embodiment, high sealing performance is achieved so that the entry of foreign objects into the optical coupling portion is prevented during disconnection, during connection, during the switch from the disconnection state to the connection state, and during the switch from the connection state to the disconnection state.

Advantageous Effects

According to the present embodiment, when the end face of the first replacement waveguide 321 and the end face of the second replacement waveguide 421 which are the optical coupling portions are damaged by foreign objects, the optical coupling portion can be easily replaced owing to the first replacement member 320 and the second replacement member 420. Moreover, in the present embodiment, owing to the above, high sealing performance can be provided so that the entry of foreign objects into the optical coupling portion is prevented during disconnection, during connection, during the switch from the disconnection state to the connection state, and during the switch from the connection state to the disconnection state.

In the present embodiment, the above can be also achieved in the first waveguide 311 and the first replacement waveguide 321 which are the optical coupling portions and in the second waveguide 411 and the second replacement waveguide 421 which are the optical coupling portions.

In the present embodiment, the distal end portion of the first positioning member 501 which functions as the protrusion portion is inserted to the replacement insertion slot portion 425 of the second replacement member 420, and engages with the replacement insertion slot portion 425. Therefore, in the present embodiment, the first holding member 310 side and the second holding member 410 side can be easily connected.

In the present embodiment, the first holding member 310 is not connected directly to the second holding member 410, but the first holding member 310 is connected to the second holding member 410 via the first replacement member 320 and the second replacement member 420. Therefore, the first replacement member 320 and the second replacement member 420 can prevent damage to the end face of the first holding member 310 including the first waveguide 311 and the end face of the first replacement member 320 including the first replacement waveguide 321, and prevent the adhesion of foreign objects to these end faces, during the switch from the disconnection state to the connection state and the switch from the connection state to the disconnection state in the first holding member 310 and the second holding member 410.

In the present embodiment, the end faces of the first holding member 310, the first replacement member 320, the second holding member 410, and the second replacement member 420 can be polished as described above. Thus, in the present embodiment, even if foreign objects adhere to the end face, the foreign objects can be removed by polishing, and these members can be reused. Therefore, according to the present embodiment, costs can be reduced.

In the present embodiment, $Tf > Lf + Lm - Tm$ ... Equation (1) and $Lm > Tm$ ... Equation (2) ensure that the distal end portion of the first positioning member 501 can protrude from the replacement insertion slot portion 325 and that the distal end portion can be inserted to and engaged with the replacement insertion slot portion 425.

In the present embodiment, the first replacement member 320 can be attached to the first holding member 310 without displacement owing to the first catching portion 327 and the first attachment member 330. The first catching portion 327 and the first attachment member 330 are provided point-symmetrically with respect to the first waveguide 311. This ensures that forces opposing each other act in a planar direction of the end face of the first replacement member 320, and the displacement of the first replacement member 320 relative to the first holding member 310 in the planar direction can be prevented. The simple configuration having the groove portion and the first claw portion 331 enables the first replacement member 320 to be attached to the first holding member 310 without displacement. The first claw portion 331 having a press force ensures that the first replacement member 320 can be attached to the first holding member 310. The above holds true with the second catching portion 427 and the second attachment member 430.

In the present embodiment, the proximal end portion of the first attachment member 330 is fixed to the first holding member 310. Thus, in the present embodiment, it is possible to prevent the displacement of the first attachment member 330 including the first claw portion 331, and ensure that forces opposing each other act in the planar direction of the end face of the first replacement member 320. This also holds true with the second attachment member 430 for the most part.

A state in which the second holding member 410 side is provided in the connector 41a as in the present embodiment is a state 1. A state in which the second holding member 410 side is provided in the plug 130a of the light source device 130 in contrast with the present embodiment is a state 2. Normally, the endoscope 10 including the connector 41a is sterilized, disinfected, and washed. When sterilized, disinfected, and washed, the endoscope 10 can be more easily cleaned in the state 1 than in the state 2. An old replacement member can be more easily replaced with a new replacement member in the state 1 than in the state 2. When the dirt adhere replacement insertion slot portion 325, the replacement insertion slot portion 325 can be more easily, for example, ultrasonically cleaned in the state 1 than in the state 2, to remove the dirt.

In the present embodiment, the first holding member 310 side is incorporated in, for example, the plug 130a. The second holding member 410 side is incorporated in, for example, the connector 41a. However, this limitation is arbitrary.

The first holding member 310 side may be incorporated in, for example, the connector 41a. In this case, the second holding member 410 side is incorporated in, for example, the plug 130a.

Thus, one of the first holding member 310 side and the second holding member 410 side has only to be incorporated in one of the plug 130a and the connector 41a, and the other of the first holding member 310 side and the second holding member 410 side has only to be incorporated in the other of the plug 130a and the connector 41a.

[Modifications of the Arrangement of Replacement Member, Attachment Member, and Positioning Mechanism 500]

[Replacement Member]

Although the first replacement member 320 is attached to the first holding member 310 and the second replacement member 420 is attached to the second holding member 410 in the present embodiment, this limitation is arbitrary.

The replacement member has only to have a replacement waveguide which is optically coupled to the first waveguide 311 and the second waveguide 411. The replacement member has only to be provided to be able to replace at least one of the first holding member 310 and the second holding member 410. The replacement member has only to intervene between the first holding member 310 and the second holding member 410 so that the replacement waveguide intervenes between the first waveguide 311 and the second waveguide 411 and is optically coupled to the first waveguide 311 and the second waveguide 411.

More specifically, the replacement member has only to be provided in at least the optical coupling portion of the optical connector 200. This optical coupling portion includes at least the end face of the first waveguide 311, and the end face of the second waveguide 411 which is optically coupled to the end face of the first waveguide 311. Therefore, the replacement member has only to intervene between the end face of the first holding member 310 and end face of the second holding member 410 which faces the end face of the first holding member 310 in the longitudinal axis direction of the optical connector 200 so that the replacement waveguide of the replacement member intervenes between the end face of the first waveguide 311 and the end face of the second waveguide 411 in the longitudinal axis direction of the optical connector 200.

[Attachment Member]

In accordance with the above arrangement of the replacement member, the attachment member has only to press the replacement member toward, for example, the side to which the replacement member is attached; for example, toward the first holding member 310 so that the replacement member is attached to at least one of the first holding member 310 and the second holding member 410.

[Positioning Mechanism 500]

In accordance with the above arrangement of the replacement member, the positioning mechanism 500 has only to position the first holding member 310, the second holding member 410 and the replacement member relative to one another so that the replacement waveguide is optically coupled to the first waveguide 311 and the second waveguide 411.

The positioning mechanism 500 has a protrusion portion which is provided on the first holding member 310 side and which protrudes from the first holding member 310 or protrudes from the replacement member attached to the first holding member 310. The protrusion portion is inserted to the second holding member 410 or to the second replacement member 420 attached to the second holding member 410 so that the first holding member 310 side is inserted to the second holding member 410 side. This protrusion portion has, for example, the distal end portion of the first positioning member 501.

[Example of the Arrangement of Replacement Member, Attachment Member, and Positioning Mechanism 500]

A specific example of the arrangement of the replacement member, the attachment member, and the positioning mechanism 500 is described below as first to fourth modifications.

First Modification

Configuration

Figure 3A:
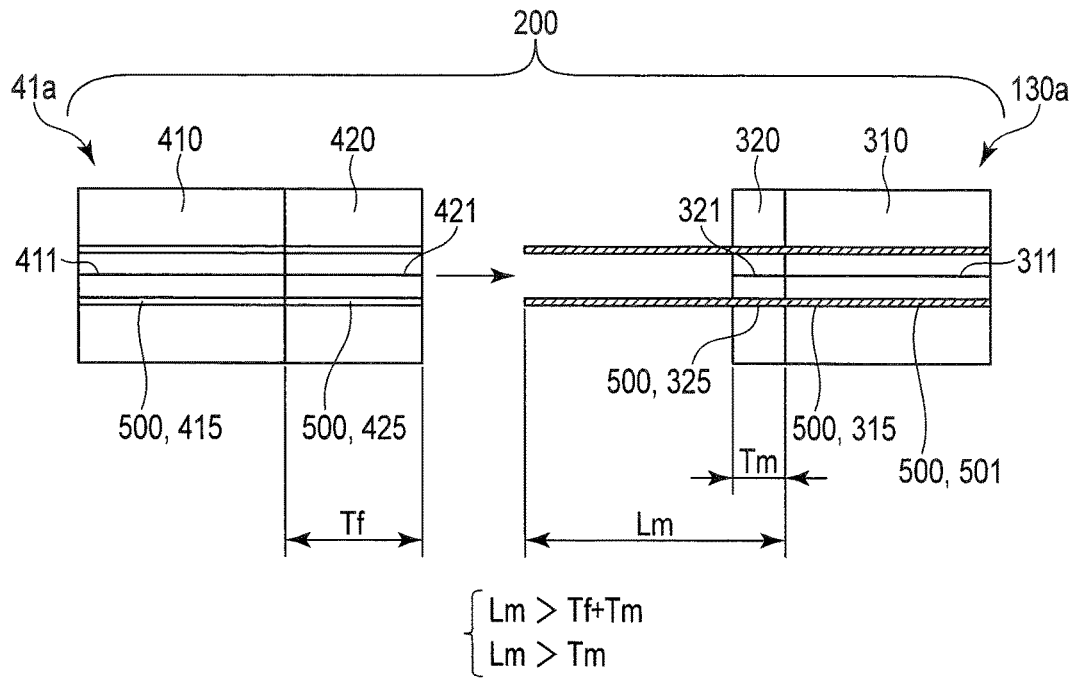
FIG. 3A is a diagram showing a first modification of the optical connector, showing the relation between the lengths Tm, Lm, and Tf, and showing how a first replacement waveguide is optically uncoupled from a second replacement waveguide in a state where a first waveguide is optically coupled to the first replacement waveguide.
Figure 3B:
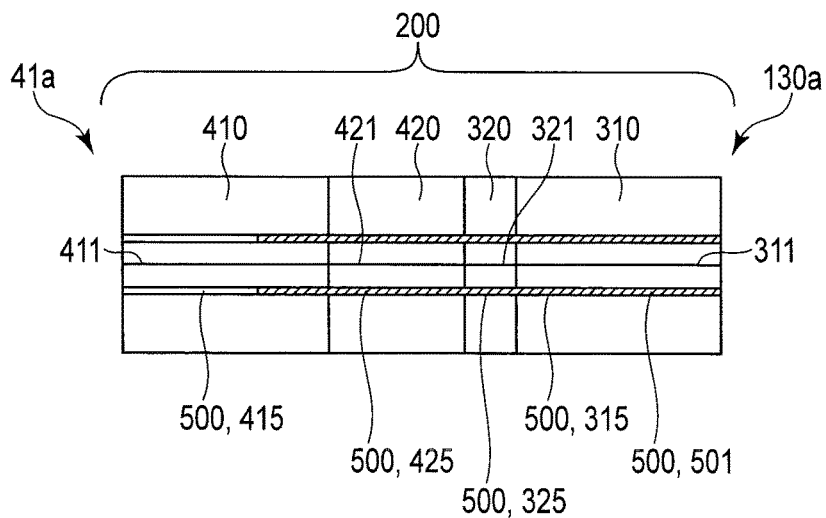
FIG. 3B is a diagram showing how the first replacement waveguide is optically coupled to the second replacement waveguide from the state shown in FIG. 3A.

As in the first embodiment, as shown in FIGS. 3A and 3B, the replacement member is attached to both the first holding member 310 and the second holding member 410. Thus, the first attachment member 330, the second attachment member 430, the first catching portion 327, and the second catching portion 427 are provided as in the first embodiment. The configurations and functions of the first attachment member 330, the second attachment member 430, the first catching portion 327, and the second catching portion 427 are similar to those in the first embodiment, and are therefore neither shown in the drawings nor described in the present modification.

As in the first embodiment, the length of the first replacement member 320 which is attached to the first holding member 310 is smaller than the length of the second replacement member 420 which is attached to the second holding member 410.

As in the first embodiment, the positioning mechanism 500 positions the first holding member 310, the second holding member 410, the first replacement member 320, and the second replacement member 420 relative to one another so that the first waveguide 311 is optically coupled to the first replacement waveguide 321 of the first replacement member 320, so that the second waveguide 411 is optically coupled to the second replacement waveguide 421 of the second replacement member 420, and so that the first replacement waveguide 321 is optically coupled to the second replacement waveguide 421.

As shown in FIG. 3A and FIG. 3B, the positioning mechanism 500 has the insertion slot portion 315, the replacement insertion slot portion 325, the insertion slot portion 415, the replacement insertion slot portion 425, and the first positioning member 501 which engages with the insertion slot portion 315, the replacement insertion slot portion 325, the insertion slot portion 415, and the replacement insertion slot portion 425.

As shown in FIG. 3A, the first positioning member 501 engages with the insertion slot portion 315 and the replacement insertion slot portion 325 so that the distal end portion of the first positioning member 501 which functions as the protrusion portion passes through the replacement insertion slot portion 325 via the insertion slot portion 315 when the first replacement waveguide 321 is optically uncoupled from the second replacement waveguide 421 while the first waveguide 311 is optically coupled to the first replacement waveguide 321.

In the present modification, the second positioning member 503 is not provided as in the present embodiment. Thus, in the state shown in FIG. 3A, in the present modification, an unshown second attachment member 430 attaches the second replacement member 420 to the second holding member 410 so that the smooth end face of the second replacement member 420 comes into abutment with and into close contact with the smooth end face of the second holding member 410, so that the second waveguide 411 is provided in alignment with the second replacement waveguide 421 in the axial direction of the optical connector 200, so that the second waveguide 411 is optically coupled to the second replacement waveguide 421, and so that the insertion slot portion 415 communicates with the replacement insertion slot portion 425 in the axial direction of the optical connector 200.

As shown in FIG. 3B, the first positioning member 501 engages with the insertion slot portion 315, the replacement insertion slot portion 325, the insertion slot portion 415, and the replacement insertion slot portion 425 so that the distal end portion of the first positioning member 501 which passes through the replacement insertion slot portion 325 is inserted to the insertion slot portion 415 via the replacement insertion slot portion 425 when the first replacement waveguide 321 is optically coupled to the second replacement waveguide 421 and the second replacement waveguide 421 is optically coupled to the second waveguide 411 while the first waveguide 311 is optically coupled to the first replacement waveguide 321.

Here,
the length of the replacement insertion slot portion 325 is referred to as Tm,
the length of the distal end portion of the first positioning member 501 which functions as the protrusion portion protruding from the insertion slot portion 315 is referred to as Lm, and
the length of the replacement insertion slot portion 425 is referred to as Tf.

When the positioning mechanism 500 positions the first holding member 310, the second holding member 410, the first replacement member 320, and the second replacement member 420 relative to one another, Equations (11), (12), and (13) below are satisfied in the present embodiment.

$$Lm > Tf + Tm \qquad \text{Equation (11)}$$

$$Lm > Tm \qquad \text{Equation (12)}$$

$$Tf > Tm \qquad \text{Equation (13)}$$

Advantageous Effects

According to the present modification, the second positioning member 503 can be omitted, so that the configuration and the assembly of the optical connector 200 can be simpler. Moreover, in the present modification, the second positioning member 503 can be omitted, so that the second replacement member 420 can be quickly replaced.

Second Modification

In contrast with the first embodiment, as shown in FIGS. 4A and 4B, the replacement member is attached to the first holding member 310 alone. Thus, the first attachment member 330 and the first catching portion 327 are provided as in the first embodiment. The configurations and functions of the first attachment member 330 and the first catching portion 327 are similar to those in the first embodiment, and are therefore neither shown in the drawings nor described in the present modification.

In contrast with the first embodiment, the positioning mechanism 500 positions the first holding member 310, the second holding member 410, and the first replacement member 320 relative to one another so that the first waveguide 311 is optically coupled to the first replacement waveguide 321 of the first replacement member 320 and the second waveguide 411 is optically coupled to the first replacement waveguide 321 of the first replacement member 320.

As shown in FIG. 4A and FIG. 4B, in contrast with the first embodiment, the positioning mechanism 500 has the insertion slot portion 315, the replacement insertion slot portion 325, the insertion slot portion 415, and the first positioning member 501 which engages with the insertion slot portion 315, the replacement insertion slot portion 325, and the insertion slot portion 415.

As shown in FIG. 4A, the first positioning member 501 engages with the insertion slot portion 315 and the replacement insertion slot portion 325 so that the distal end portion of the first positioning member 501 which functions as the protrusion portion passes through the replacement insertion slot portion 325 via the insertion slot portion 315 when the second waveguide 411 is optically uncoupled from the first replacement waveguide 321 while the first waveguide 311 is optically coupled to the first replacement waveguide 321.

As shown in FIG. 4B, the first positioning member 501 engages with the insertion slot portion 315, the replacement insertion slot portion 325, and the insertion slot portion 415 so that the distal end portion of the first positioning member 501 which passes through the replacement insertion slot portion 325 is inserted to the insertion slot portion 415 when the second waveguide 411 is optically coupled to the first replacement waveguide 321 while the first waveguide 311 is optically coupled to the first replacement waveguide 321.

Here, the length of the replacement insertion slot portion 325 is referred to as Tm, and the length of the distal end portion of the first positioning member 501 which functions as the protrusion portion protruding from the insertion slot portion 315 is referred to as Lm.

When the positioning mechanism 500 positions the first holding member 310, the second holding member 410, and the first replacement member 320 relative to one another, Equation (21) below is satisfied in the present embodiment.

$$Lm > Tm \qquad \text{Equation (21)}$$

Advantageous Effects

According to the present modification, the second replacement member 420 and the second positioning member 503 can be omitted, so that the configuration and the assembly of the optical connector 200 can be simpler.

Third Modification

Figure 5A:
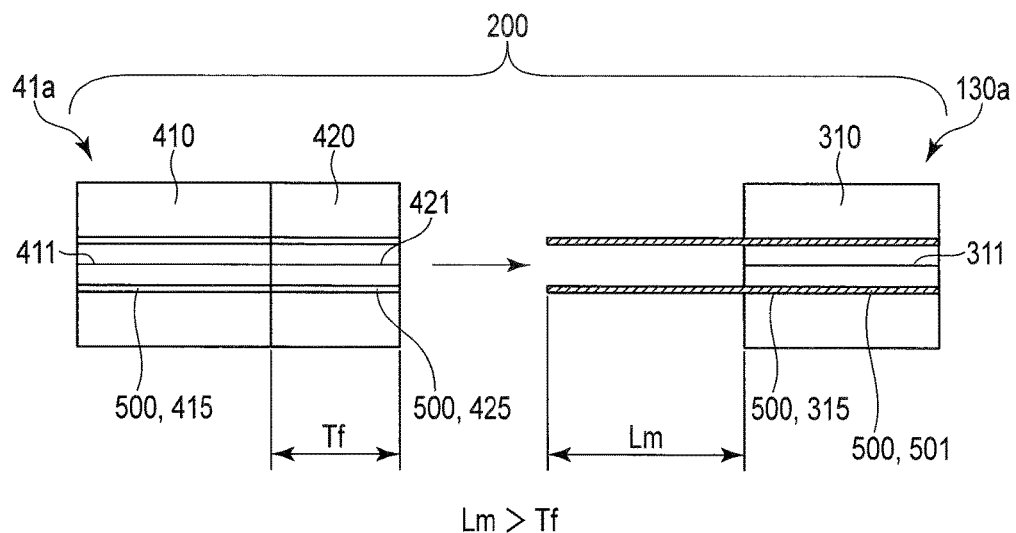
FIG. 5A is a diagram showing a third modification of the optical connector, showing the relation between the lengths Lm and Tf, and showing how a first waveguide is optically uncoupled from a second replacement waveguide.
Figure 5B:
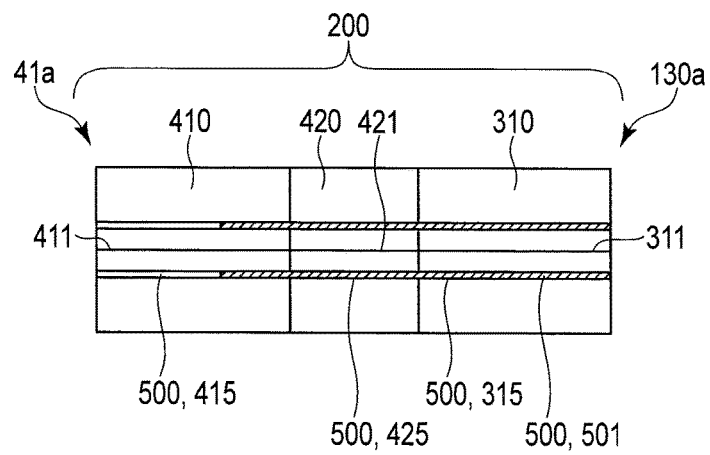
FIG. 5B is a diagram showing how the first waveguide is optically coupled to the second replacement waveguide from the state shown in FIG. 5A.

In contrast with the first embodiment, as shown in FIGS. 5A and 5B, the replacement member is attached to the second holding member 410 alone. Thus, the second attachment member 430 and the second catching portion 427 are provided as in the first embodiment. The configurations and functions of the second attachment member 430 and the second catching portion 427 are similar to those in the first embodiment, and are therefore neither shown in the drawings nor described in the present modification.

In contrast with the first embodiment, the positioning mechanism 500 positions the first holding member 310, the second holding member 410, and the second replacement member 420 relative to one another so that the first waveguide 311 is optically coupled to the second replacement waveguide 421 of the second replacement member 420 and the second waveguide 411 is optically coupled to the second replacement waveguide 421 of the second replacement member 420.

As shown in FIG. 5A and FIG. 5B, in contrast with the first embodiment, the positioning mechanism 500 has the insertion slot portion 315, the insertion slot portion 415, the replacement insertion slot portion 425, and the first positioning member 501 which engages with the insertion slot portion 315, the replacement insertion slot portion 425, and the insertion slot portion 415.

As shown in FIG. 5A, the first positioning member 501 engages with the insertion slot portion 315 so that the distal end portion of the first positioning member 501 which functions as the protrusion portion passes through the insertion slot portion 315 when the first waveguide 311 is optically uncoupled from the second replacement waveguide 421.

In the present modification, the second positioning member 503 is not provided as in the present embodiment. Thus, in the state shown in FIG. 5A, in the present modification, the unshown second attachment member 430 attaches the second replacement member 420 to the second holding member 410 so that the smooth end face of the second replacement member 420 comes into abutment with and into close contact with the smooth end face of the second holding member 410, so that the second waveguide 411 is provided in alignment with the second replacement waveguide 421 in the axial direction of the optical connector 200, so that the second waveguide 411 is optically coupled to the second replacement waveguide 421, and so that the insertion slot portion 415 communicates with the replacement insertion slot portion 425 in the axial direction of the optical connector 200.

As shown in FIG. 5B, the first positioning member 501 engages with the insertion slot portion 315, the replacement insertion slot portion 425, and the insertion slot portion 415 so that the distal end portion of the first positioning member 501 which passes through the insertion slot portion 315 is inserted to the insertion slot portion 415 via the replacement insertion slot portion 425 when the first waveguide 311 is optically coupled to the second replacement waveguide 421 and the second replacement waveguide 421 is optically coupled to the second waveguide 411.

Here, the length of the distal end portion of the first positioning member 501 which functions as the protrusion portion protruding from the insertion slot portion 315 is referred to as Lm, and the length of the replacement insertion slot portion 425 is referred to as Tf.

When the positioning mechanism 500 positions the first holding member 310, the second holding member 410, and the second replacement member 420 relative to one another, Equation (31) below is satisfied in the present modification.

$$Lm > Tf \qquad \text{Equation (31)}$$

Advantageous Effects

According to the present modification, the first replacement member 320 and the second positioning member 503 can be omitted, so that the configuration and the assembly of the optical connector 200 can be simpler. Moreover, according to the present modification, the second positioning member 503 can be omitted, so that the second replacement member 420 can be quickly replaced.

Fourth Modification

Figure 6A:
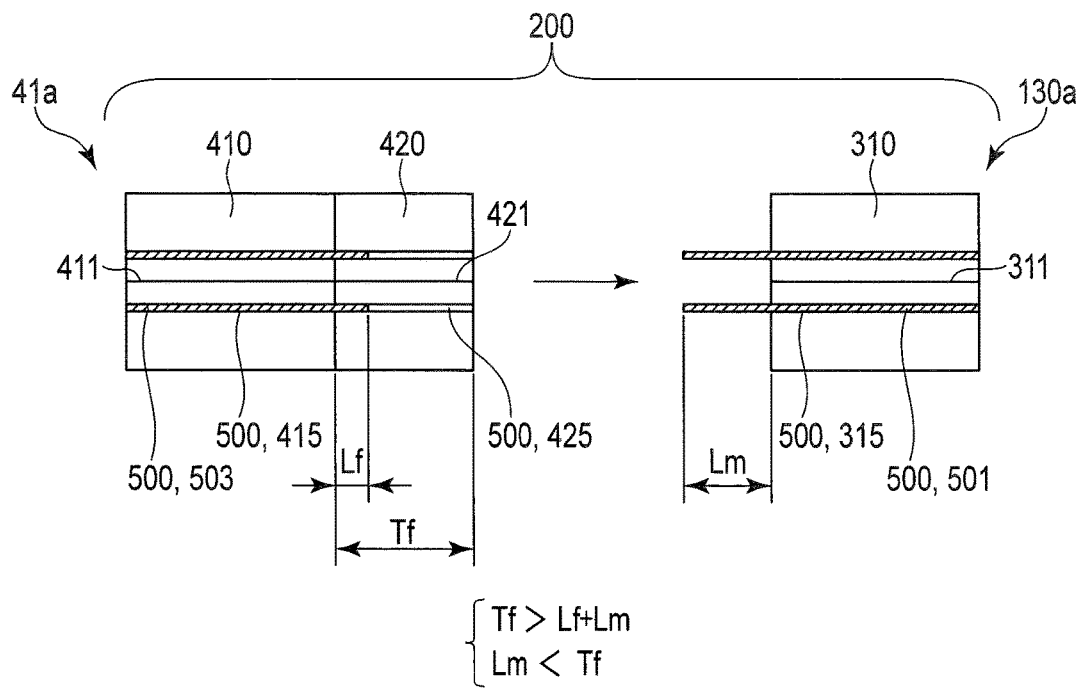
FIG. 6A is a diagram showing a fourth modification of the optical connector, showing the relation between lengths Tm, Tf, and Lf, and showing how a first waveguide is optically uncoupled from a second replacement waveguide.
Figure 6B:
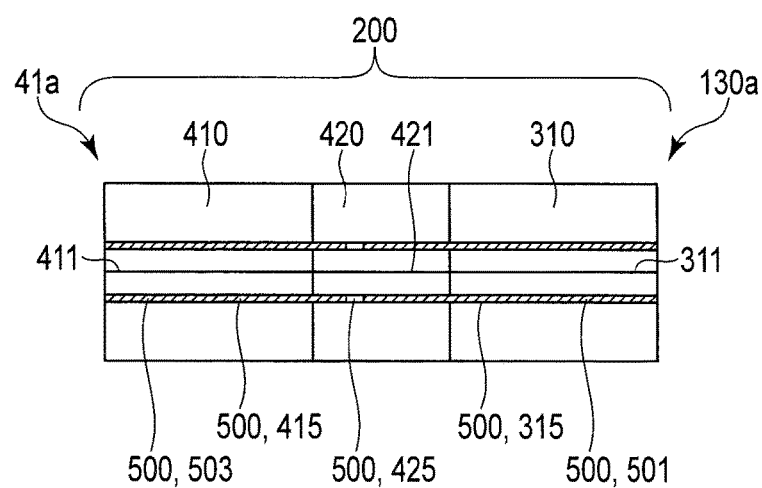
FIG. 6B is a diagram showing how the first waveguide is optically coupled to the second replacement waveguide from the state shown in FIG. 6A.

In contrast with the first embodiment, as shown in FIGS. 6A and 6B, the replacement member is attached to the second holding member 410 alone. Thus, the second attachment member 430 and the second catching portion 427 are provided as in the first embodiment. The configurations and functions of the second attachment member 430 and the second catching portion 427 are similar to those in the first embodiment, and are therefore neither shown in the drawings nor described in the present modification.

In contrast with the first embodiment, the positioning mechanism 500 positions the first holding member 310, the second holding member 410, and the second replacement member 420 relative to one another so that the first waveguide 311 is optically coupled to the second replacement waveguide 421 of the second replacement member 420 and the second waveguide 411 is optically coupled to the second replacement waveguide 421 of the second replacement member 420.

As shown in FIG. 6A and FIG. 6B, in contrast with the first embodiment, the positioning mechanism 500 has the insertion slot portion 315, the insertion slot portion 415, the replacement insertion slot portion 425, the first positioning member 501 which engages with the insertion slot portion 315 and the replacement insertion slot portion 425, and the second positioning member 503 which engages with the insertion slot portion 415 and the replacement insertion slot portion 425.

As shown in FIG. 6A, the first positioning member 501 engages with the insertion slot portion 315 so that the distal end portion of the first positioning member 501 which functions as the protrusion portion passes through the insertion slot portion 315 when the first waveguide 311 is optically uncoupled from the second replacement waveguide 421.

As shown in FIG. 6B, the first positioning member 501 engages with the insertion slot portion 315 and the replacement insertion slot portion 425 so that the distal end portion of the first positioning member 501 which passes through the insertion slot portion 315 is inserted to the replacement insertion slot portion 425 when the first waveguide 311 is optically coupled to the second replacement waveguide 421 while the second waveguide 411 is optically coupled to the second replacement waveguide 421.

As shown in FIG. 6A and FIG. 6B, the second positioning member 503 engages with the insertion slot portion 415 and the replacement insertion slot portion 425 so that the second waveguide 411 is optically coupled to the second replacement waveguide 421.

Here, the length of the distal end portion of the first positioning member 501 functioning as the protrusion protruding from the insertion slot portion 315 is referred to as Lm, the length of the replacement insertion slot portion 425 is referred to as Tf, and the length of the protrusion portion of the second positioning member 503 protruding from the insertion slot portion 415 is referred to as Lf.

When the positioning mechanism 500 positions the first holding member 310, the second holding member 410, and the second replacement member 420 relative to one another, Equations (41) and (42) below are satisfied in the present modification.

$$Tf > Lf + Lm \quad \text{Equation (41)}$$

$$Lm < Tf \quad \text{Equation (42)}$$

Advantageous Effects

According to the present modification, the first replacement member 320 can be omitted, so that the configuration and the assembly of the optical connector 200 can be simpler.

Other Modifications

Modifications other than those of the above arrangement of the replacement members 320 and 420, the attachment members 330 and 430, and the positioning mechanism 500 are described below.

Fifth Modification

Figure 7A:
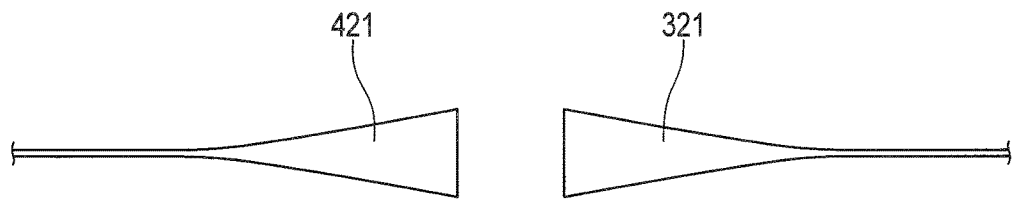
FIG. 7A is a diagram showing a fifth modification of the optical connector, and showing that a replacement waveguide has a taper fiber.
Figure 7B:
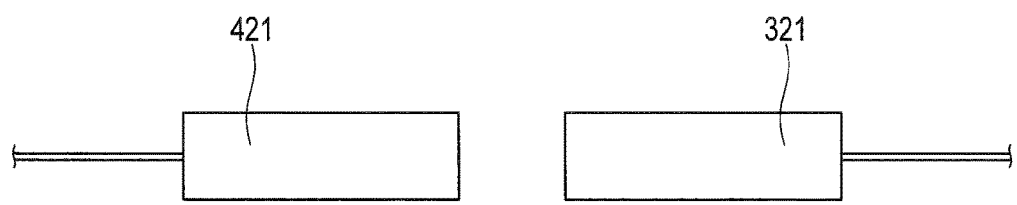
FIG. 7B is a diagram showing the fifth modification of the optical connector, and showing that a replacement waveguide has a lens.

Each of the replacement waveguides 321 and 421 has only to have one of an optical fiber, a taper fiber shown in FIG. 7A, and a lens shown in FIG. 7B.

The diameter of the taper fiber provided in the first replacement waveguide 321 gradually decreases, for example, toward the first holding member 310 from the second replacement member 420 as shown in FIG. 7A. The diameter of the taper fiber provided in the second replacement waveguide 421 gradually decreases, for example, toward the second holding member 410 from the first replacement member 320 as shown in FIG. 7A.

As shown in FIG. 7B, the lens has, for example, a GRIN lens in which the refractive index in the center of the lens is higher than the refractive index in the circumference of the lens.

Thus, the replacement waveguide has only to have an optical element.

Sixth Modification

Figure 8:
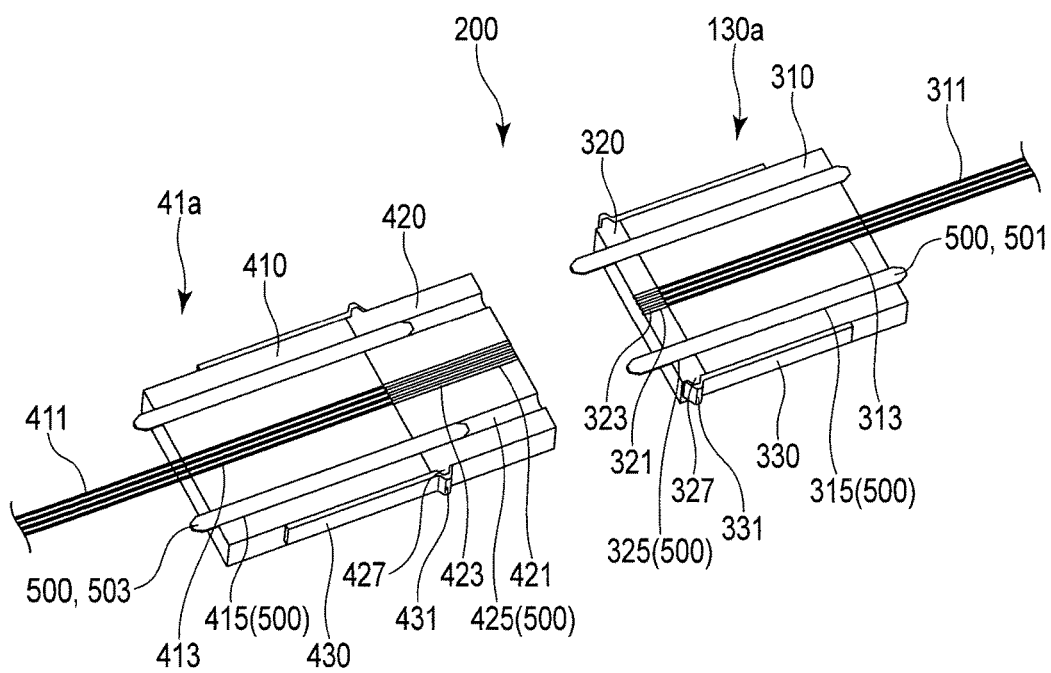
FIG. 8 is a diagram showing a sixth modification of the optical connector, and showing that a catching portion has a protrusion portion.

As shown in FIG. 8, each of the catching portions 327 and 427 may have a protrusion portion. The protrusion portion is integral with, for example, the side surface of each of the replacement members 320 and 420, and perpendicularly protrudes from the side surface toward the side of the optical connector 200.

Thus, each of the catching portions 327 and 427 has only to have one of a groove portion and a protrusion portion. The groove portion does not need to be depressed perpendicularly to the side surface of each of the replacement members 320 and 420, and may be, for example, inclined.

The present invention is not completely limited to the embodiments described above, and modifications of components can be made at the stage of carrying out the invention without departing from the spirit thereof. Further, various inventions can be made by properly combining the components disclosed in the embodiments described above.

What is claimed is:

1. An optical connector for an endoscope comprising:
    a first holding member which holds a first waveguide therein;
    a second holding member which holds a second waveguide therein;
    a replaceable replacement member which has a replacement waveguide that is optically coupled to the first waveguide and the second waveguide and which intervenes between the first holding member and the second holding member so that the replacement waveguide intervenes between the first waveguide and the second waveguide and is optically coupled to the first waveguide and the second waveguide;
    an attachment member which presses the replacement member toward a side to which the replacement member is attached so that the replacement member is attached to at least one of the first holding member and the second holding member; and
    a positioning mechanism which positions the first holding member, the second holding member, and the replacement member relative to one another so that the replacement waveguide is optically coupled to the first waveguide and the second waveguide;
    wherein the positioning mechanism has a protrusion portion which is provided on the first holding member side and which protrudes from the first holding member or protrudes from the replacement member attached to the first holding member, and
    the protrusion portion is inserted to the second holding member or to the replacement member attached to the second holding member so that the first holding member side is inserted to the second holding member side.

2. The optical connector for the endoscope according to claim 1, wherein an end face of the replacement member is configured to be polished together with an end face of the replacement waveguide while the replacement member is holding the replacement waveguide so that the end face of the replacement member is provided flush with the end face of the replacement waveguide and so that the end face of the replacement member and the end face of the replacement waveguide are smoothed.

3. The optical connector for the endoscope according to claim 2, wherein the replacement member is attached to both the first holding member and the second holding member,
the length of a first replacement member which is attached to the first holding member is smaller than the length of a second replacement member which is attached to the second holding member,
the positioning mechanism positions the first holding member, the second holding member, the first replacement member, and the second replacement member relative to one another so that the first waveguide is optically coupled to a first replacement waveguide of the first replacement member, so that the second waveguide is optically coupled to a second replacement waveguide of the second replacement member, and so that the first replacement waveguide is optically coupled to the second replacement waveguide, and
the positioning mechanism comprises
a first holding side insertion slot portion provided in the first holding member,
a first replacement side insertion slot portion provided in the first replacement member,
a second holding side insertion slot portion provided in the second holding member,
a second replacement side insertion slot portion provided in the second replacement member,
a first positioning member, the first positioning member engaging with the first holding side insertion slot portion and the first replacement side insertion slot portion so that a distal end portion of the first positioning member which functions as the protrusion portion passes through the first replacement side insertion slot portion via the first holding side insertion slot portion when the first replacement waveguide is optically uncoupled from the second replacement waveguide while the first waveguide is optically coupled to the first replacement waveguide, the first positioning member engaging with the first holding side insertion slot portion, the first replacement side insertion slot portion, and the second replacement side insertion slot portion so that the distal end portion which passes through the first replacement side insertion slot portion is inserted to the second replacement side insertion slot portion when the first replacement waveguide is optically coupled to the second replacement waveguide while the first waveguide is optically coupled to the first replacement waveguide, and
a second positioning member which engages with the second holding side insertion slot portion and the second replacement side insertion slot portion so that the second waveguide is optically coupled to the second replacement waveguide.

4. The optical connector for the endoscope according to claim 3, wherein when the positioning mechanism positions the first holding member, the second holding member, the first replacement member, and the second replacement member relative to one another, the following equations are satisfied:

$$Tf > Lf + Lm - Tm, \text{ and}$$

$$Lm > Tm,$$

in which the length of the first replacement side insertion slot portion is referred to as Tm,
the length of the distal end portion of the first positioning member which functions as the protrusion portion protruding from the first holding side insertion slot portion is referred to as Lm,
the length of the second replacement side insertion slot portion is referred to as Tf, and
the length of a protrusion portion of the second positioning member protruding from the second holding side insertion slot portion is referred to as Lf.

5. The optical connector for the endoscope according to claim 2, wherein the replacement member is attached to both the first holding member and the second holding member,
the length of a first replacement member which is attached to the first holding member is smaller than the length of a second replacement member which is attached to the second holding member,
the positioning mechanism positions the first holding member, the second holding member, the first replacement member, and the second replacement member relative to one another so that the first waveguide is optically coupled to a first replacement waveguide of the first replacement member, so that the second waveguide is optically coupled to a second replacement waveguide of the second replacement member, and so that the first replacement waveguide is optically coupled to the second replacement waveguide, and
the positioning mechanism comprises
a first holding side insertion slot portion provided in the first holding member,
a first replacement side insertion slot portion provided in the first replacement member,
a second holding side insertion slot portion provided in the second holding member,
a second replacement side insertion slot portion provided in the second replacement member, and
a first positioning member, the first positioning member engaging with the first holding side insertion slot portion and the first replacement side insertion slot portion so that a distal end portion of the first positioning member which functions as the protrusion portion passes through the first replacement side insertion slot portion via the first holding side insertion slot portion when the first replacement waveguide is optically uncoupled from the second replacement waveguide while the first waveguide is optically coupled to the first replacement waveguide, the first positioning member engaging with the first holding side insertion slot portion, the first replacement side insertion slot portion, the second holding side insertion slot portion, and the second replacement side insertion slot portion so that the distal end portion which passes through the first replacement side insertion slot portion is inserted to the second holding side insertion slot portion via the second replacement side insertion slot portion when the first replacement waveguide is optically coupled to the second replacement waveguide and the second replacement waveguide is optically coupled to the second waveguide while the first waveguide is optically coupled to the first replacement waveguide.

6. The optical connector for the endoscope according to claim 5, wherein when the positioning mechanism positions the first holding member, the second holding member, the first replacement member, and the second replacement member relative to one another, the following equations are satisfied:

$$Lm > Tf + Tm, \text{ and}$$

$$Lm > Tm,$$

in which the length of the first replacement side insertion slot portion is referred to as Tm,
the length of the distal end portion of the first positioning member which functions as the protrusion portion protruding from the first holding side insertion slot portion is referred to as Lm, and
the length of the second replacement side insertion slot portion is referred to as Tf.

7. The optical connector for the endoscope according to claim 2, wherein the replacement member is attached to the first holding member,
the positioning mechanism positions the first holding member, the second holding member, and the replacement member relative to one another so that the first waveguide is optically coupled to the replacement waveguide of the replacement member and the second waveguide is optically coupled to the replacement waveguide of the replacement member, and
the positioning mechanism comprises
a first holding side insertion slot portion provided in the first holding member,
a replacement side insertion slot portion provided in the replacement member,
a second holding side insertion slot portion provided in the second holding member, and
a first positioning member, the first positioning member engaging with the first holding side insertion slot portion and the replacement side insertion slot portion so that a distal end portion of the first positioning member which functions as the protrusion portion passes through the replacement side insertion slot portion via the first holding side insertion slot portion when the second waveguide is optically uncoupled from the replacement waveguide while the first waveguide is optically coupled to the replacement waveguide, the first positioning member engaging with the first holding side insertion slot portion, the replacement side insertion slot portion, and the second holding side insertion slot portion so that the distal end portion which passes through the replacement side insertion slot portion is inserted to the second holding side insertion slot portion when the second waveguide is optically coupled to the replacement waveguide while the first waveguide is optically coupled to the replacement waveguide.

8. The optical connector for the endoscope according to claim 7, wherein when the positioning mechanism positions the first holding member, the second holding member, and the replacement member relative to one another, the following equation is satisfied:

$$Lm > Tm,$$

in which the length of the replacement side insertion slot portion is referred to as Tm, and
the length of the distal end portion of the first positioning member which functions as the protrusion portion protruding from the first holding side insertion slot portion is referred to as Lm.

9. The optical connector for the endoscope according to claim 2, wherein the replacement member is attached to the second holding member,
the positioning mechanism positions the first holding member, the second holding member, and the replacement member relative to one another so that the first waveguide is optically coupled to the replacement waveguide of the replacement member and the second waveguide is optically coupled to the replacement waveguide of the replacement member, and
the positioning mechanism comprises
a first holding side insertion slot portion provided in the first holding member,
a second holding side insertion slot portion provided in the second holding member,
a replacement side insertion slot portion provided in the replacement member, and
a first positioning member, the first positioning member engaging with the first holding side insertion slot portion so that a distal end portion of the first positioning member which functions as the protrusion portion passes through the first holding side insertion slot portion when the first waveguide is optically uncoupled from the replacement waveguide, the first positioning member engaging with the first holding side insertion slot portion, the replacement side insertion slot portion, and the second holding side insertion slot portion so that the distal end portion which passes through the first holding side insertion slot portion is inserted to the second holding side insertion slot portion via the replacement side insertion slot portion when the first waveguide is optically coupled to the replacement waveguide and the replacement waveguide is optically coupled to the second waveguide.

10. The optical connector for the endo scope according to claim 9, wherein when the positioning mechanism positions the first holding member, the second holding member, and the replacement member relative to one another, the following equation is satisfied:

$$Lm > Tf,$$

in which the length of the distal end portion of the first positioning member which functions as the protrusion portion protruding from the first holding side insertion slot portion is referred to as Lm, and
the length of the replacement side insertion slot portion is referred to as Tf.

11. The optical connector for the endoscope according to claim 2, wherein the replacement member is attached to the second holding member,
the positioning mechanism positions the first holding member, the second holding member, and the replacement member relative to one another so that the first waveguide is optically coupled to the replacement waveguide of the replacement member and the second waveguide is optically coupled to the replacement waveguide of the replacement member, and
the positioning mechanism comprises
a first holding side insertion slot portion provided in the first holding member,
a second holding side insertion slot portion provided in the second holding member, a replacement side insertion slot portion provided in the replacement member, a first positioning member, the first positioning member engaging with the first holding side insertion slot portion so that a distal end portion of the first positioning member which functions as the protrusion portion passes through the first holding side insertion slot portion when the first waveguide is optically uncoupled from the replacement waveguide, the first positioning member engaging with the first holding side insertion slot portion and the replacement side insertion slot portion so that the distal end portion which passes through the first holding side insertion slot portion is inserted to the replacement side insertion slot portion when the first waveguide is optically coupled to the replacement waveguide while the second waveguide is optically coupled to the replacement waveguide, and a second positioning member which engages with the second holding side insertion slot portion and the replacement side insertion slot portion so that the second waveguide is optically coupled to the replacement waveguide.

12. The optical connector for the endoscope according to claim 11, wherein when the positioning mechanism positions the first holding member, the second holding member, and the replacement member relative to one another, the following equations are satisfied:

$$Tf > Lf + Lm, \text{ and}$$

$$Lm < Tf,$$

in which the length of the distal end portion of the first positioning member which functions as the protrusion portion protruding from the first holding side insertion slot portion is referred to as Lm, the length of the replacement side insertion slot portion is referred to as Tf, and the length of a protrusion portion of the second positioning member protruding from the second holding side insertion slot portion is referred to as Lf.

13. The optical connector for the endoscope according to claim 1, wherein the replacement waveguide has one of an optical fiber, a taper fiber, and a lens.

14. The optical connector for the endoscope according to claim 1, wherein the attachment member has a claw portion provided at a distal end portion of the attachment member, the claw portion being caught on the replacement member, and when caught, pressing the replacement member toward the side to which the replacement member is attached.

15. The optical connector for the endoscope according to claim 1, wherein the attachment member is provided in an attachment side to which the replacement member is attached so that the attachment member is provided point-symmetrically with respect to a waveguide provided on the attachment side.

16. The optical connector for the endoscope according to claim 1, wherein more than one replacement waveguide is provided.

17. The optical connector for the endoscope according to claim 1, wherein one of the first holding member side and the second holding member side is incorporated in one of a plug of an apparatus, and a connector which is provided in a universal cord of the endoscope and which is plugged into the plug, and the other of the first holding member side and the second holding member side is incorporated in the other of the plug and the connector.

18. An optical connector for an endoscope comprising:
a first holding member which holds a first waveguide therein;
a second holding member which holds a second waveguide therein;
a replaceable replacement member which has a replacement waveguide that is optically coupled to the first waveguide and the second waveguide and which intervenes between the first holding member and the second holding member so that the replacement waveguide intervenes between the first waveguide and the second waveguide and is optically coupled to the first waveguide and the second waveguide;
an attachment member which presses the replacement member toward a side to which the replacement member is attached so that the replacement member is attached to at least one of the first holding member and the second holding member; and
a positioning mechanism which positions the first holding member, the second holding member, and the replacement member relative to one another so that the replacement waveguide is optically coupled to the first waveguide and the second waveguide;
wherein the replacement member has a catching portion which is formed in a circumferential surface of the replacement member and on which a distal end portion of the attachment member is caught.

19. The optical connector for the endoscope according to claim 18, wherein the catching portion is provided point-symmetrically with respect to the replacement waveguide.

20. An optical connector for an endoscope comprising:
a first holding member which holds a first waveguide therein;
a second holding member which holds a second waveguide therein;
a replaceable replacement member which has a replacement waveguide that is optically coupled to the first waveguide and the second waveguide and which intervenes between the first holding member and the second holding member so that the replacement waveguide intervenes between the first waveguide and the second waveguide and is optically coupled to the first waveguide and the second waveguide;
an attachment member which presses the replacement member toward a side to which the replacement member is attached so that the replacement member is attached to at least one of the first holding member and the second holding member; and
a positioning mechanism which positions the first holding member, the second holding member, and the replacement member relative to one another so that the replacement waveguide is optically coupled to the first waveguide and the second waveguide;
wherein the attachment member has a proximal end portion fixed to the circumferential surface of the side to which the replacement member is attached.

* * * * *